US012185986B2

(12) United States Patent
Hoernschemeyer et al.

(10) Patent No.: US 12,185,986 B2
(45) Date of Patent: Jan. 7, 2025

(54) SEGMENTAL TENSIONING OF SPINAL TETHERS

(71) Applicant: OrthoPediatrics Corp., Warsaw, IN (US)

(72) Inventors: Daniel Gerard Hoernschemeyer, Columbia, MO (US); Matthew Prygoski, North Liberty, IN (US); Evangelos Tozakoglou, Fort Wayne, IN (US)

(73) Assignee: OrthoPediatrics Corp., Warsaw, IN (US)

(*) Notice: Subject to any disclaimer, the term of this patent is extended or adjusted under 35 U.S.C. 154(b) by 1238 days.

(21) Appl. No.: 16/625,498

(22) PCT Filed: Jan. 30, 2019

(86) PCT No.: PCT/US2019/015828
§ 371 (c)(1),
(2) Date: Dec. 20, 2019

(87) PCT Pub. No.: WO2019/152502
PCT Pub. Date: Aug. 8, 2019

(65) Prior Publication Data
US 2020/0360059 A1    Nov. 19, 2020

Related U.S. Application Data

(60) Provisional application No. 62/623,769, filed on Jan. 30, 2018.

(51) Int. Cl.
A61B 17/70    (2006.01)

(52) U.S. Cl.
CPC ...... *A61B 17/7053* (2013.01); *A61B 17/7022* (2013.01); *A61B 17/7031* (2013.01); *A61B 17/7059* (2013.01)

(58) Field of Classification Search
CPC .............. A61B 17/7019; A61B 17/702; A61B 17/7022; A61B 17/7026; A61B 17/7029;
(Continued)

(56) References Cited

U.S. PATENT DOCUMENTS 5,387,213 A * 2/1995 Breard ................. A61F 2/0811
606/256
5,704,936 A * 1/1998 Mazel ................ A61B 17/7044
606/255
(Continued)

FOREIGN PATENT DOCUMENTS

GB    2244775 A    12/1991

OTHER PUBLICATIONS

PCT/US19/15828, Search Report and Written Opinion, 15 pgs Apr. 23, 2019.

*Primary Examiner* — Lynnsy M Summitt
(74) *Attorney, Agent, or Firm* — Gerald W. Roberts; John V. Daniluck; Dentons Bingham Greenebaum LLP

(57) ABSTRACT

Implantable devices for dynamic interconnection between bones, and especially between vertebrae. The devices provide for various types of manipulation of a flexible connection such as a tether, such as by providing an aperture through which the flexible connection is passed and guided, or a post to which a loop of the flexible connection can be attached, or a groove in which a loop of the flexible connection can be placed.

12 Claims, 16 Drawing Sheets

(58) Field of Classification Search
CPC ............ A61B 17/7031; A61B 17/7053; A61B 17/7007; A61B 17/7044; A61B 17/842
See application file for complete search history.

(56) References Cited

U.S. PATENT DOCUMENTS

| | | | |
|---|---|---|---|
| 5,725,582 A * | 3/1998 | Bevan | A61B 17/842 623/13.12 |
| 6,149,653 A | 11/2000 | Deslauriers | |
| 6,248,106 B1 * | 6/2001 | Ferree | A61B 17/7022 606/328 |
| 6,299,613 B1 * | 10/2001 | Ogilvie | A61B 17/0642 606/279 |
| 6,325,805 B1 * | 12/2001 | Ogilvie | A61B 17/0644 606/911 |
| 6,436,099 B1 | 8/2002 | Drewry et al. | |
| 6,551,320 B2 * | 4/2003 | Lieberman | A61B 17/701 606/86 R |
| 6,802,844 B2 * | 10/2004 | Ferree | A61B 17/705 606/259 |
| 7,285,121 B2 * | 10/2007 | Braun | A61B 17/864 606/279 |
| 7,658,751 B2 | 2/2010 | Stone et al. | |
| 8,177,810 B2 * | 5/2012 | Ferree | A61B 17/8861 606/264 |
| 8,211,151 B2 * | 7/2012 | Schwab | A61B 17/7022 606/264 |
| 8,231,654 B2 | 7/2012 | Kaiser et al. | |
| 9,078,644 B2 * | 7/2015 | Stone | A61B 17/842 |
| 9,271,713 B2 | 3/2016 | Denham et al. | |
| 9,642,661 B2 | 5/2017 | Stone et al. | |
| 2002/0007184 A1 | 1/2002 | Ogilvie et al. | |
| 2002/0133155 A1 * | 9/2002 | Ferree | A61B 17/7031 606/264 |
| 2004/0147928 A1 | 7/2004 | Landry et al. | |
| 2005/0038428 A1 | 2/2005 | Kelman et al. | |
| 2005/0267470 A1 * | 12/2005 | McBride | A61B 17/7022 606/279 |
| 2007/0112352 A1 | 5/2007 | Sorensen | |
| 2008/0200956 A1 | 8/2008 | Beckwith et al. | |
| 2008/0300599 A1 | 12/2008 | Anapliotis et al. | |
| 2009/0264932 A1 | 10/2009 | Alamin et al. | |
| 2009/0292318 A1 | 11/2009 | White et al. | |
| 2010/0063550 A1 | 3/2010 | Felix et al. | |
| 2010/0137908 A1 | 6/2010 | Zhang | |
| 2010/0160968 A1 | 6/2010 | Joshi et al. | |
| 2010/0292736 A1 | 11/2010 | Schwab | |
| 2011/0276096 A1 | 11/2011 | Erickson et al. | |
| 2011/0319945 A1 | 12/2011 | Tepic | |
| 2012/0016423 A1 | 1/2012 | Hua | |
| 2012/0035671 A1 | 2/2012 | Hodge et al. | |
| 2012/0109111 A1 | 5/2012 | Li | |
| 2013/0253587 A1 | 9/2013 | Carls et al. | |
| 2016/0128732 A1 | 5/2016 | Strnad et al. | |
| 2016/0278762 A1 | 9/2016 | Hodge et al. | |
| 2017/0007299 A1 | 1/2017 | Mundis, Jr. et al. | |

* cited by examiner

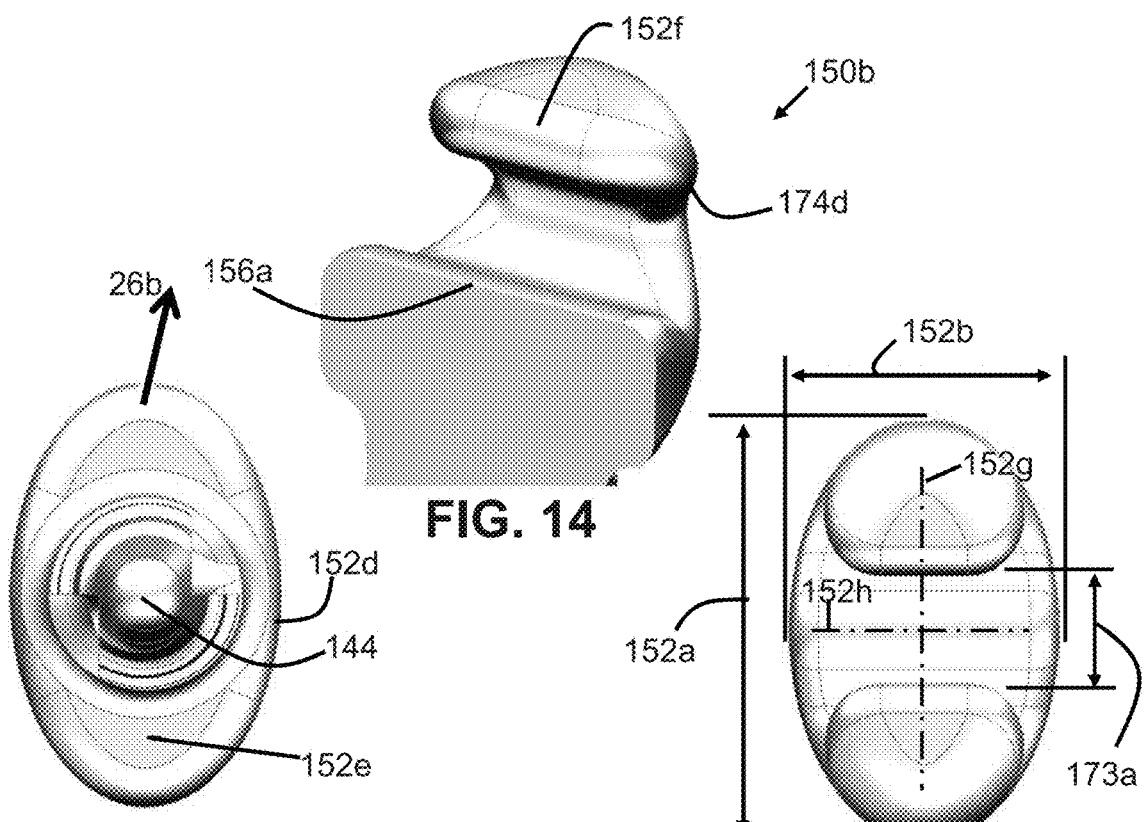
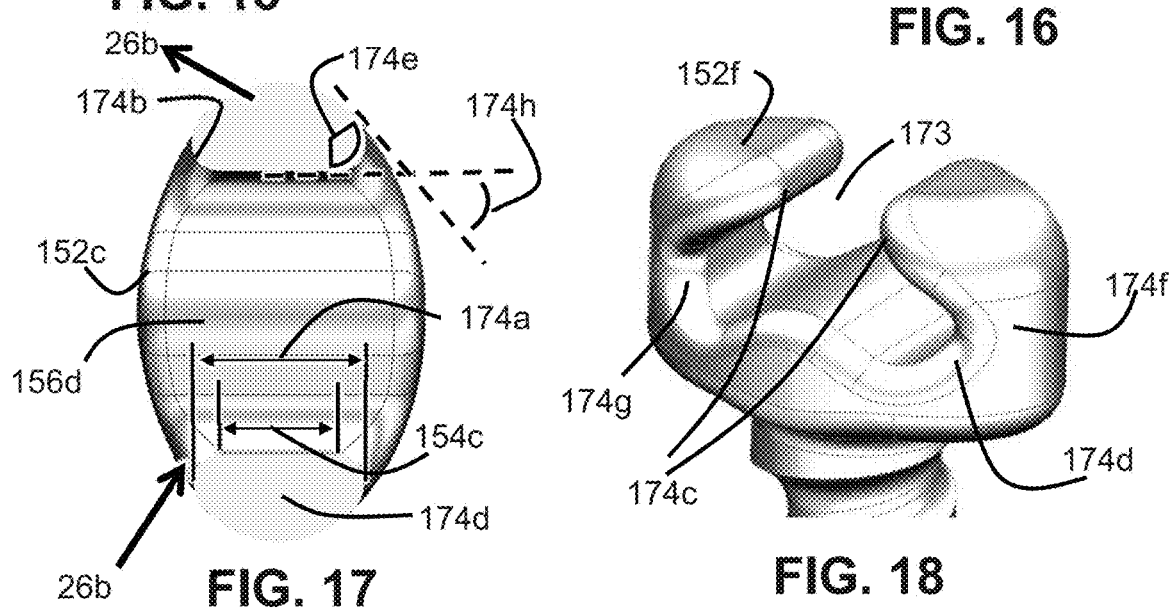

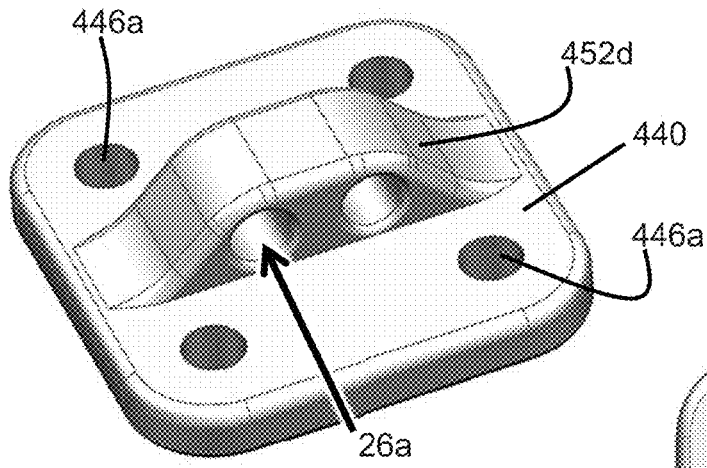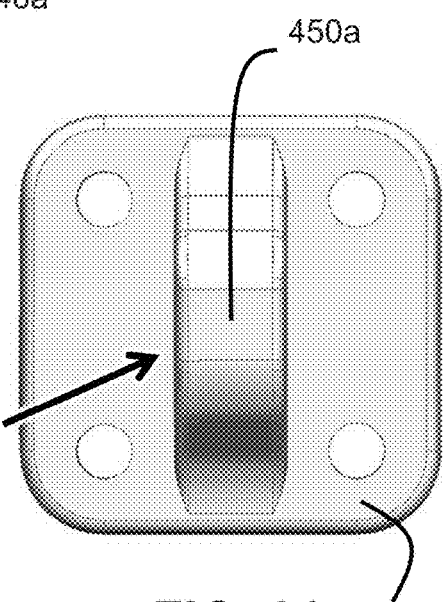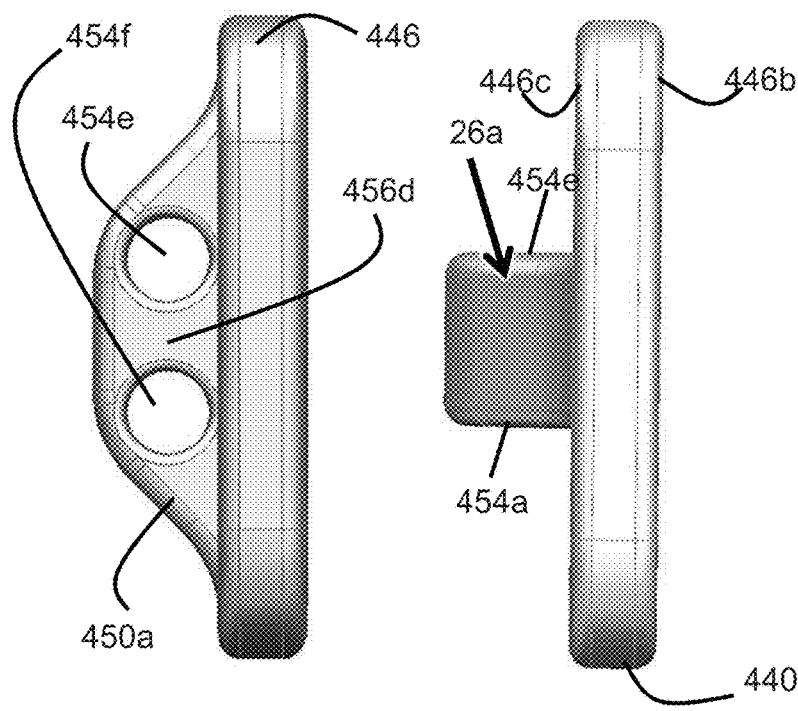
FIG. 28
FIG. 29  FIG. 30  FIG. 31

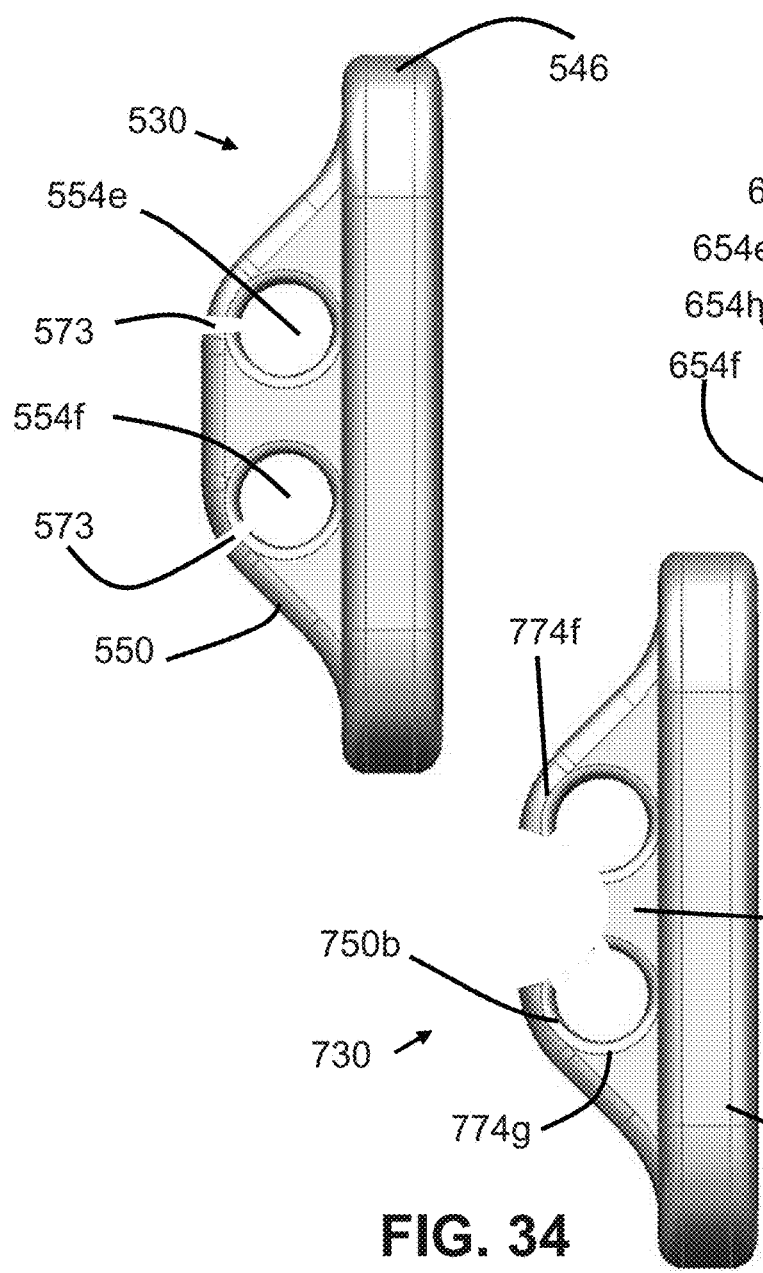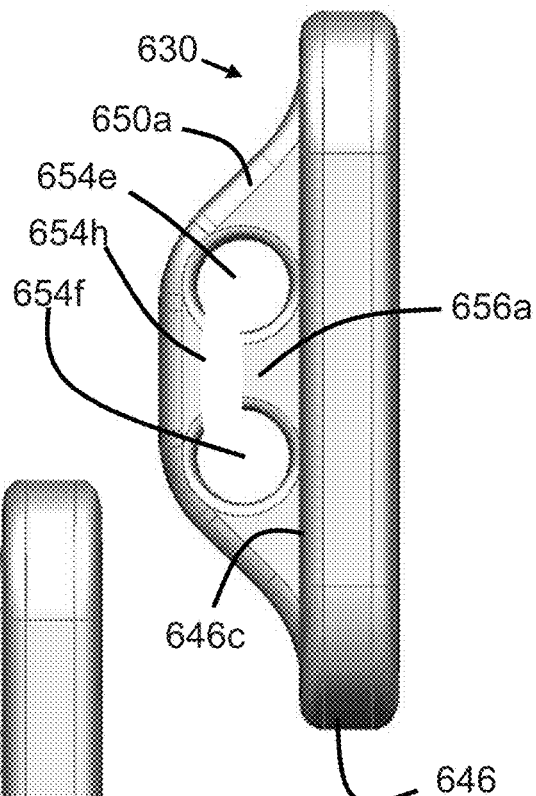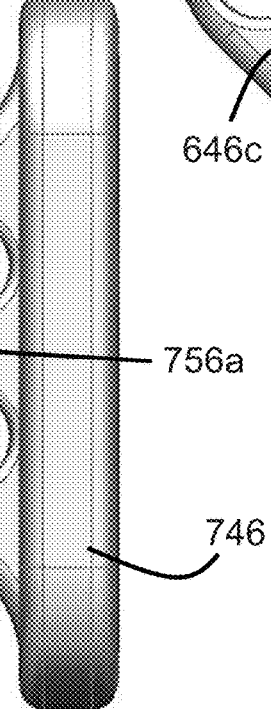
FIG. 32
FIG. 33
FIG. 34

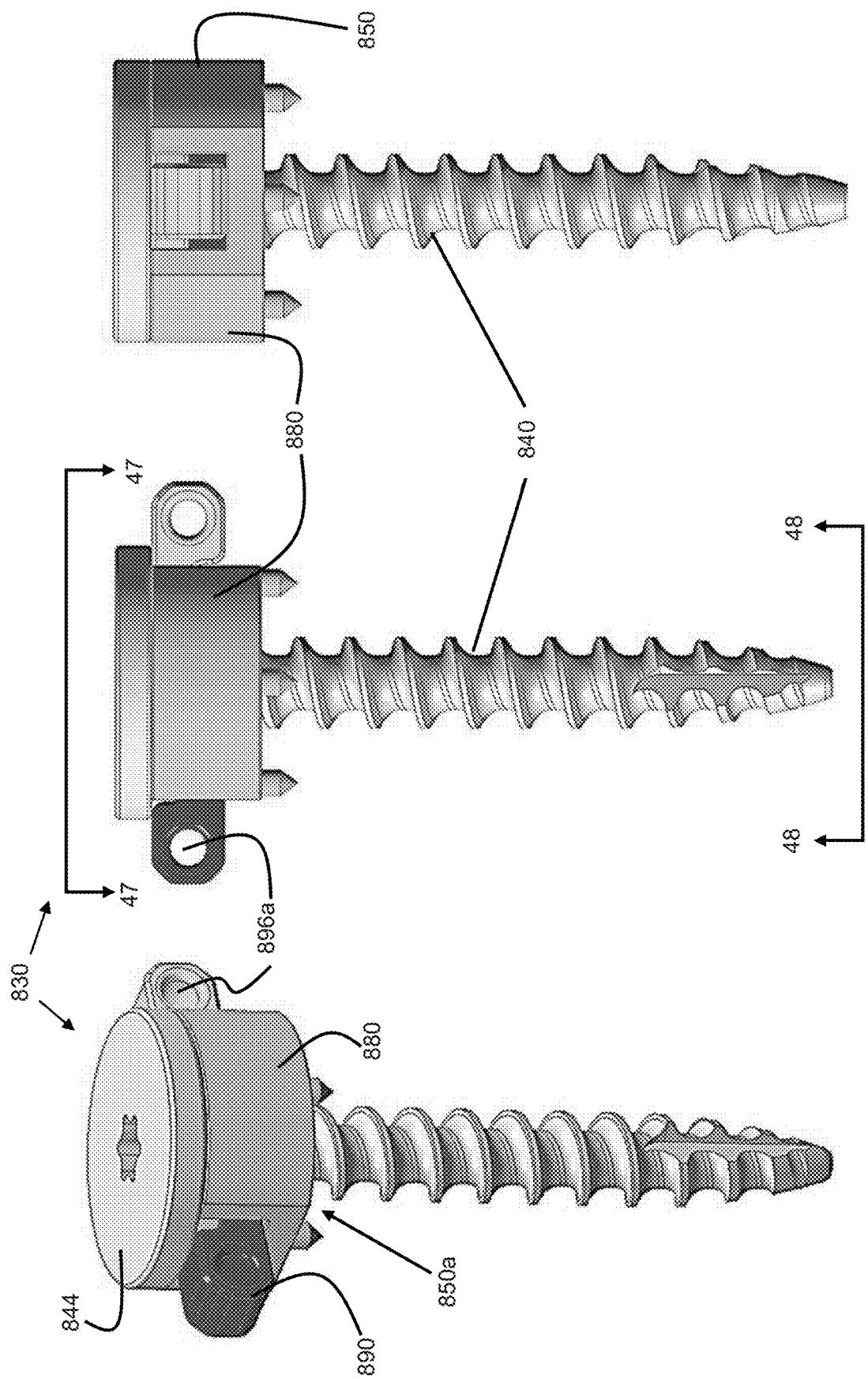

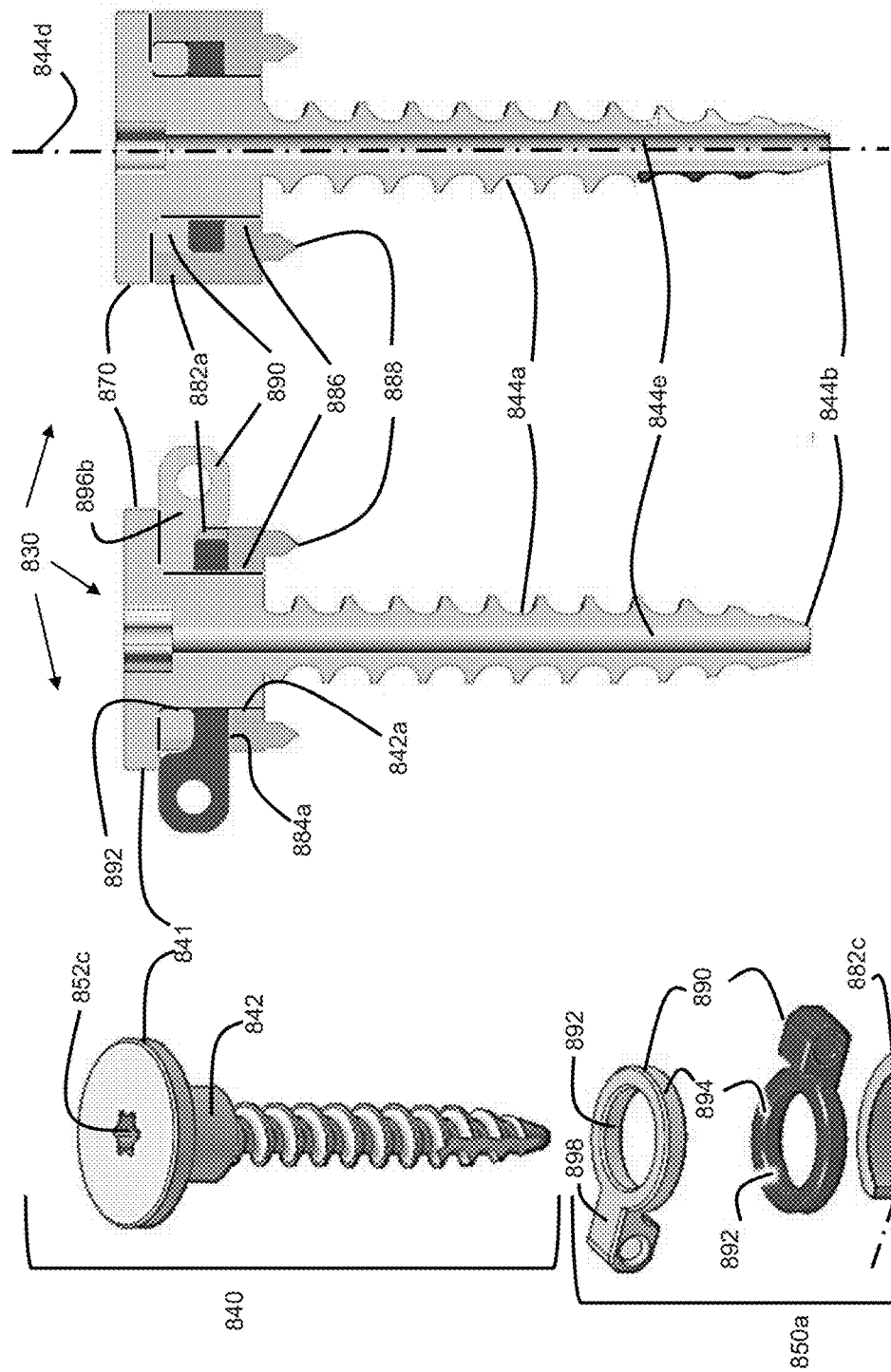

SEGMENTAL TENSIONING OF SPINAL TETHERS

CROSS REFERENCE TO RELATED APPLICATION

This application claims the benefit of priority to U.S. Provisional Patent Application Ser. No. 62/623,769, filed Jan. 30, 2018, incorporated herein by reference.

FIELD OF THE INVENTION

Various embodiments of the present invention pertain to apparatus and methods for securing two objects by a flexible connection, and in other embodiments the interconnection of two vertebrae or other bones with a flexible connection, such as a tether or sutures.

BACKGROUND OF THE INVENTION

Vertebral body tethering (VBT) remains a procedure in the experimental phase. The behavior of long bone physes are well known and the effects of guided growth fairly predictable. This is not the case with the spine. Each vertebra has 2 end plates, acting as growth plates. How they respond to guided growth is not yet predictable. Previous work by Betz with the Nitinol staple and other authors shed some light on the topic. However, questions such as amount of tension, segmental differences in tension (and alteration over time under load) and the long term effects on the discs remain unanswered.

SUMMARY OF THE INVENTION

One aspect of the present invention pertains to a member for connection to a vertebra. Some embodiments include a head. Other embodiments include means for connecting the head to a vertebra. Still further embodiments include means for coupling the head to a flexible material.

Examples of flexible materials include suture and tethers fabricated from organic materials, and metallic wires. In some embodiments, the flexible material provides a non-rigid connection between two different members, with the flexible material capable of sustaining tension between the members, but substantially not capable of sustaining compression between the members. Tethers of any cross-sectional shape are contemplated, including substantially circular cross sections, elongate cross sections, square cross sections, and flat cross sections.

Another aspect of the present invention pertains to a member for tethered connection to a bone. Some embodiments include a bone connecting member adapted and configured for connection with a vertebra. Other embodiments include a head attached to the bone connecting member, the head including first and second passageways extending across the head; each passageway being adapted and configured to accept therein a corresponding first or second tether, each passageway having an entrance on one side of the head and an exit on the opposing side of the head, each passageway being enclosed from the top surface of the head, the head including a smoothly contoured convex lower surface that partially separates the first passageway from the second passageway.

Yet another aspect of the present invention pertains to a member for tethered connection to a bone. Some embodiments include a bone connecting member adapted and configured for connection with a vertebra. Other embodiments include a head attached to the bone connecting member, the head including first and second spaced apart securement posts each adapted and configured for connection to a loop of a flexible tether, each post including a groove sized to accept therein a tether loop, each groove having an angular extent for placement of the loop.

Still another aspect of the present invention pertains to a member for tethered connection to a bone. Some embodiments include a bone connecting member adapted and configured for connection with a vertebra. Other embodiments include a head attached to the bone connecting member, the head including first and second spaced apart peripheral grooves each adapted and configured for connection to a separate loop of flexible tether, the head having a top surface furthest away from the vertebrae, wherein one of the peripheral grooves is between the other peripheral groove and the vertebra.

Another aspect of the present invention pertains to a method for tethering of vertebrae. Some embodiments include attaching a first tethering head to a first vertebra, attaching a second tethering head to the first vertebra spaced apart from the first tethering head, and attaching a third tethering head to a second vertebra. Other embodiments of the present invention include looping one end of a first flexible tether in a first groove in the first tethering head and looping one end of a second flexible tether in a second groove in the second tethering head. Still other embodiments pertain to connecting the first vertebra to the second vertebra by looping the other end of the first flexible tether within a groove in the third tethering head; and connecting the first vertebra to the second vertebra by looping the other end of the second flexible tether within a groove in the third tethering head Yet another aspect of the present invention pertains to a method for tethering of vertebrae. Some embodiments include attaching a first tethering head to a first vertebra and attaching a second tethering head to a second vertebra. Other embodiments include looping a flexible tether in a first groove extending around the periphery of the first tethering head. Yet other embodiments include extending the looped tether from the first tethering head to the second tethering head and passing the extension of the looped tether though an aperture in the second tethering head.

Still another aspect of the present invention pertains to a member for making a flexible connection between bones. Some embodiments include a bone connecting member adapted and configured for connection with a vertebra, the bone connecting member including an alignment feature. Some embodiments include a receiver for a flexible connector, the receiver having a body including a protrusion with a passageway for a flexible connector and including a first aperture adapted and configured to receive therein the alignment feature. Some embodiments include a head having a central pocket that receives therein the receiver, the central pocket including a aperture that permits placement of the protrusion, wherein connection of said bone connecting member to a bone captures said separable receiver within the central pocket.

Another aspect of the present invention pertains to a member for making a flexible connection between bones. Some embodiments include a connecting member having a first aligning element. Some embodiments include a first separable receiver for a flexible connector, the first receiver having a body including a first passageway for a flexible connector. Some embodiments include a second separable receiver for a flexible connector, the second receiver having a body including a second passageway for a flexible connector. Some embodiments include a head having a pocket that receives therein the first receiver and the second receiver, the pocket including a first lateral aperture that permits placement therethrough of the first passageway, the pocket including a second lateral aperture that permits placement therethrough of the second passageway, the head including a second aligning element adapted and configured to couple with said first aligning element; wherein placement of the first and second separable receivers within the central pocket permits alignment of the first aligning element with the second aligning element.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, some of the figures shown herein may have been created from scaled drawings or from photographs that are scalable. It is understood that such dimensions, or the relative scaling within a figure, are by way of example, and not to be construed as limiting. It is further understood that with regards to CAD drawings, that the figures may show additional lines that pertain to changes in the geometry of the surface, or to separate elements joined together to form the overall CAD model, as would be understood by one of ordinary skill in the art.

FIG. 14 is a cross sectional, perspective, and enlarged representation of a portion of the apparatus of FIG. 13.

FIG. 15 is an end plan view of the apparatus of FIG. 2, looking from the shank toward the head.

FIG. 16 is a top plan view of the apparatus of FIG. 2, looking from the head toward the shank.

FIG. 17 is a cross sectional view of the apparatus of FIG. 2 as taken along line 17-17 of FIG. 2.

FIG. 18 is an enlarged perspective view of a portion of the apparatus of FIG. 2.

FIG. 28 is a perspective CAD surface representation of a vertebral tethering member according to yet another embodiment of the present invention.

FIG. 29 is a side elevational view of the apparatus of FIG. 28.

FIG. 30 is an end elevational view of the apparatus of FIG. 28.

FIG. 31 is a top plan view of the apparatus of FIG. 28.

FIG. 32 is a side elevational view of a vertebral tethering member according to yet another embodiment of the present invention.

FIG. 33 is a side elevational view of a vertebral tethering member according to yet another embodiment of the present invention.

FIG. 34 is a side elevational view of a vertebral tethering member according to yet another embodiment of the present invention.

FIG. 40 is a top, side, perspective CAD representation of a vertebral tethering member according to another embodiment of the present invention.

FIG. 41 is a side elevational view of the apparatus of FIG. 40.

FIG. 42 is an end elevational view of the apparatus of FIG. 40.

FIG. 43 is an exploded perspective view of the apparatus of FIG. 40.

FIG. 44 is a cross sectional view of the apparatus of FIG. 41 as taken in the plane of FIG. 41.

FIG. 45 is a cross sectional view of the apparatus of FIG. 42 as taken in the plane of FIG. 42.

ELEMENT NUMBERING

Figure 1:
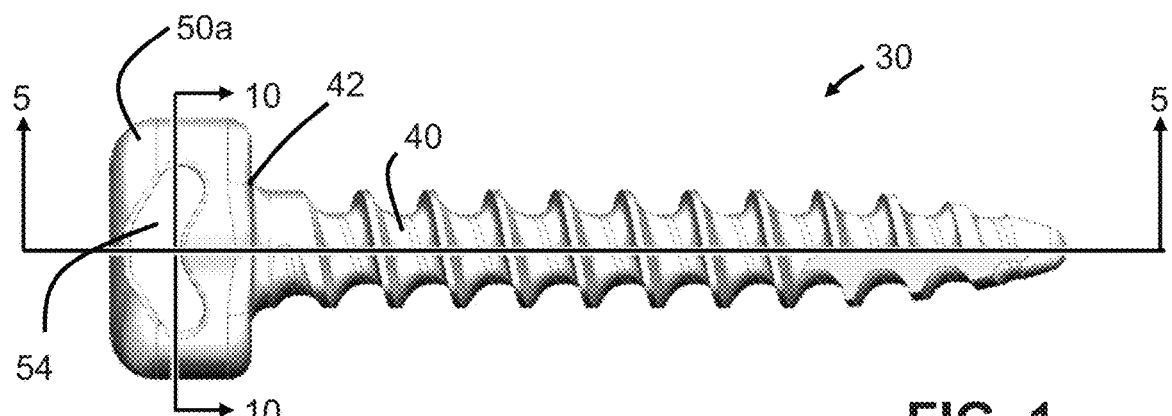
FIG. 1 is a CAD surface representation of a vertebral tethering member according to one embodiment of the present invention.

The following is a list of element numbers and at least one noun used to describe that element. It is understood that none of the embodiments disclosed herein are limited to these nouns, and these element numbers can further include other words that would be understood by a person of ordinary skill reading and reviewing this disclosure in its entirety.

| 20 | spine |
|---|---|
| 22 | vertebrae |
| 24 | Suture, cord, cable or tether; flexible connection |
| 26 | suture approach direction |
| a | guiding |
| b | hitching |
| c | looping |
| 30 | vertebral tethering member |
| a | guiding |
| b | hitching |
| c | looping |
| 40 | connecting means head to vertebra |
| 41 | Top portion |
| 42 | neck, alignment feature |
| 44 | anchor |
| a | shaft |
| b | tip |
| c | threads |
| d | central axis |
| 46 | plates |
| a | through holes; fastener holes |
| b | bone contacting surface |
| c | upper surface |
| 50 | tethering head |
| a | guiding head |
| b | hitching head |
| c | looping head |
| 52 | planform shape; oblong; circular |
| a | maximum width |
| b | central width |
| c | driving feature |
| d | smooth outer surface |
| e | underside; bone contacting surface |
| f | top surface |
| g | plane of symmetry |
| h | plane of symmetry |
| 54 | passageways |
| a | entrance |
| b | exit |
| c | width, entrance to exit |
| d | inner wall |
| e | first passageway |
| f | second passageway |
| h | top wall |
| i | bottom wall |

-continued

| 56 | floor |
|---|---|
| a | convex feature |
| b | V-shape |
| c | included angle |
| d | ridge |
| 60 | looping head |
| 64 | peripheral groove |
| a | top |
| b | bottom |
| c | width |
| d | depth |
| 70 | hitching head |
| 73 | slot or opening |
| a | width |
| 74 | securement post |
| a | maximum width |
| b | radiused edges |
| c | overhang |
| d | minimum cross sectional area |
| e | angular extent |
| f | first |
| g | second |
| h | post angle, tether approach |
| 78 | capturing head |
| 80 | receiving head; alignment head |
| 82a | sidewalls |
| b | central pocket |
| c | internal shape |
| 84a | aperture, sidewalls |
| b | axis |
| 86 | aperture, central |
| 88 | bone-contacting projections |
| 90 | washer; tethering member; flexible connection receiver |
| 92 | aperture, central |
| 94 | outer shape |
| 96a | passageway |
| b | protrusion |
| 98 | body |

DETAILED DESCRIPTION OF ONE OR MORE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention, and further permits the reasonable and logical inference of still other embodiments as would be understood by persons of ordinary skill in the art.

It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "preferably," refers to features and aspects that are present in at least one embodiment, but which are optional for some embodiments, it therefore being understood that use of the word "preferably" implies the term "optional."

The use of an N-series prefix for an element number (NXX.XX) refers to an element that is the same as the non-prefixed element (XX.XX), except as shown and described. As an example, an element 130 would be the same as element 30, except for those different features of element 130 shown and described. Further, common elements and common features of related elements may be first drawn in the same manner in different figures, and/or use the same symbology in different figures. As such, it is not necessary, as one example, to describe features of 154 and 54 that are the same, since these common features are apparent to a person of ordinary skill in the related field of technology. Further, it is understood that some features may be backward compatible, such that a feature of a later discussed embodiment (NXX.XX) may include features compatible with other various embodiments that were discussed earlier (MXX.XX), as would be understood by those of ordinary skill in the art. This description convention also applies to the use of prime ('), double prime ("), and triple prime ("') suffixed element numbers. Therefore, it is not necessary to describe the features of 20.1, 20.1', 20.1", and 20.1'" that are the same, since these common features are apparent to persons of ordinary skill in the related field of technology.

This document may use different words to describe the same element number, or to refer to an element number in a specific family of features (NXX.XX). It is understood that such multiple, different words are not intended to provide a redefinition of any language herein. It is understood that such words demonstrate that the particular feature can be considered in various linguistical ways, such ways not necessarily being additive or exclusive.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise explicitly noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

Various embodiments of the present invention pertain to different methods and apparatus for providing a flexible connection among the vertebra of a spine. Various tethering heads are shown which provide one or more of a looping attachment of one or more suturing loops, guidance of the suture loop over several vertebrae, or the hitching attachment of multiple suturing loops. Each of the tethering heads can include any acceptable means for attachment to a vertebrae. Examples shown herein include screw-type bone anchors and fastener-coupled bone plates. However, the tethering heads and tethering methods discussed herein can be attached by any method and any type of bone connection member.

Further shown herein are various methods for using one or more of the tethering heads in combination on a particular patient. As examples, looping-type or hitching-type tethering heads can be utilized for attachment of the loop itself to the tethering head. Various methods contemplate multiple tethering heads being attached to one vertebrae, and connected or guided with a single tethering head on an adjacent vertebrae. As will be shown, the tethering heads discussed herein permit the simultaneous use of one or more suturing loops across one or more vertebrae.

As the term "loops" is used herein, it references loops of any type of flexible connector, and produced in any way, including: (a) static, fixed length loops that are applied between tethering members; (b) adjustable loops that are adjusted outside of the patient and then applied between tethering members; and also (c) adjustable loops that are first applied between implanted tethering members, and subsequently tensioned and shortened so as to draw the anchors together. Loops can be fabricated from free ends of a tether in any manner, including by way of splicing; use of knots; a single attachment crimping each end together; separate crimped attachments, one for each end, with the crimped attachments being attached together; fusing, such as by heat or ultrasonics; adhesives; or any other.

Figure 2:
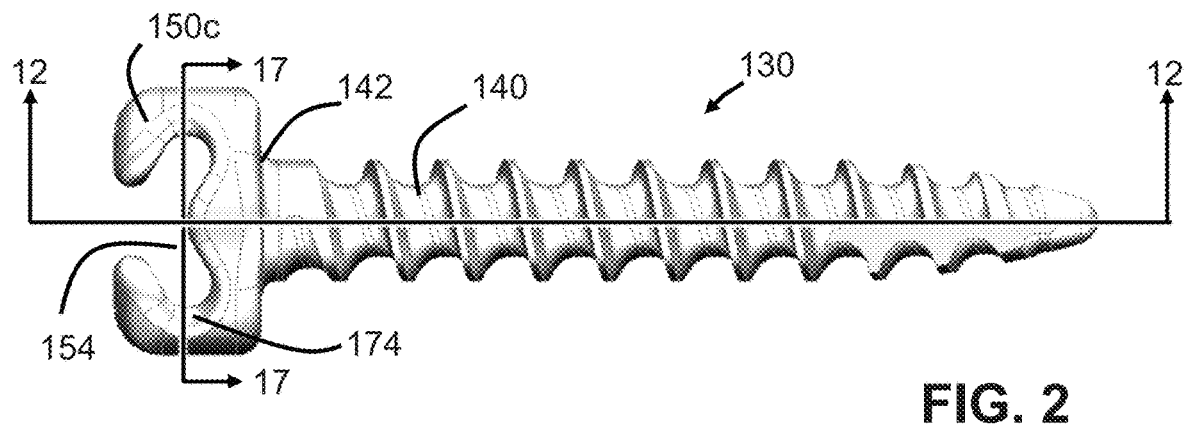
FIG. 2 is a CAD surface representation of a vertebral tethering member according to yet another embodiment of the present invention.
Figure 3:
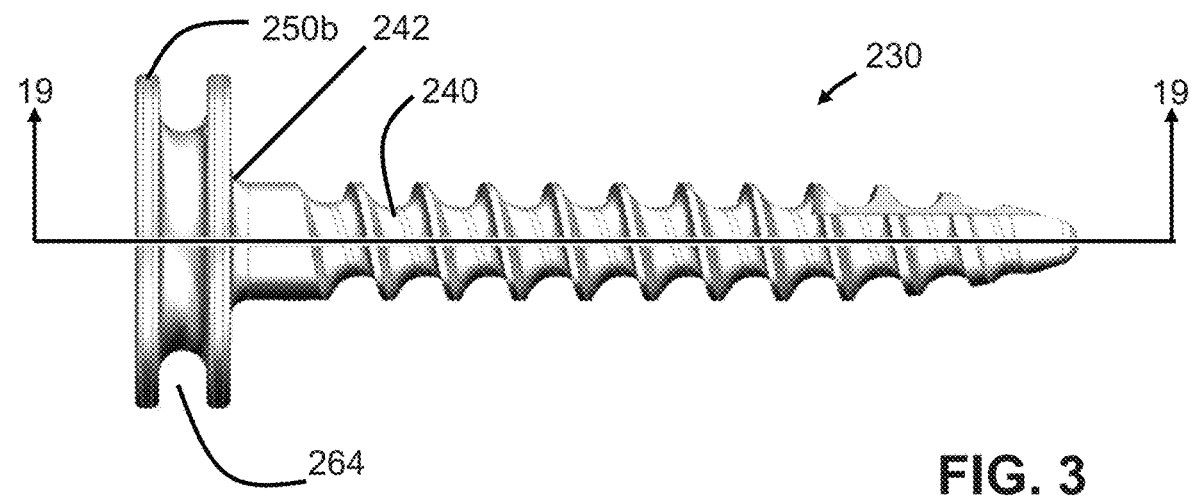
FIG. 3 is a CAD surface representation of a vertebral tethering member according to yet another embodiment of the present invention.
Figure 4:
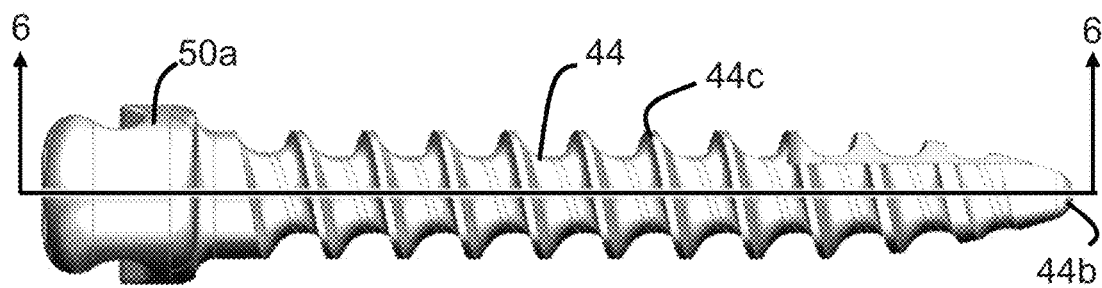
FIG. 4 is a side elevational view of the apparatus of FIG. 1.

FIGS. 1, 2, and 3 show side elevational views of vertebral tethering members 30, 130, and 230, respectively, each having tethering heads X50 according to various embodiments of the present invention. FIG. 1 shows a tethering head 50*a* that is adapted and configured to guide within the head the strands of a loop of tethering or suturing material. FIG. 2 presents a side elevational view of a tethering head 150*c* adapted and configured to provide one or more "hitching" posts that are adapted and configured to receive around each of them a loop of tethering or suturing material. FIG. 3 shows a tethering head 250*b* adapted and configured to receive in a groove around its periphery a loop of tethering or suturing material.

FIGS. 1 and 4-10 show various views of a vertebral tethering member 30 according to one embodiment of the present invention. Tethering member 30 includes a tethering head 50*a* and means 40 for connecting the head to a vertebrae. Tethering head 50*a* includes within it an upside down, enclosed V-shaped passageway 54. In the embodiment shown, connecting means 40 is an anchoring screw 44 that includes a plurality of threads 44*c* on a shaft 44*a*. Connecting means 40 extends from a neck 42 that attaches to the underside of head 50*a* to a tip 44*b* that is adapted and configured to be inserted into a hole in the vertebrae. The necks X42 shown herein preferably include increased cross sectional areas proximate to this attachment, so as to manage the distribution of stresses and forces transitioning between the head and the connection means.

As shown and described herein, means X40 for connecting a head X50 to a vertebrae can be any type of device or method that securely affixes the head X50 to the vertebrae. Examples include the anchoring screws shown in several embodiments herein, as well as a plate, post, hook, clip, or strap, as examples. In the embodiments shown, the connection means 40 includes a neck X42 that provides attachment to the underside 52*e* of the head 50.

Figure 5:
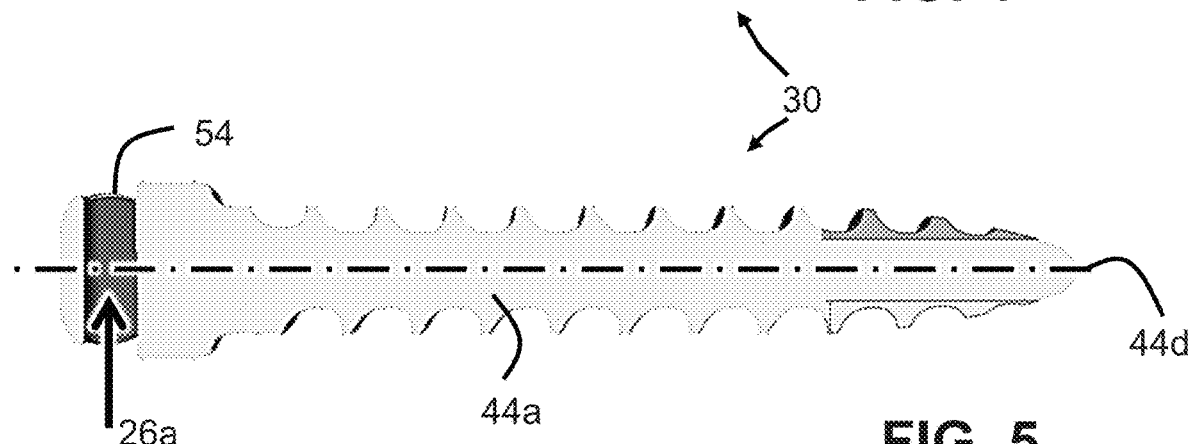
FIG. 5 is a cross sectional representation of the apparatus of FIG. 1 as taken along line 5-5 of FIG. 1.
Figure 6:
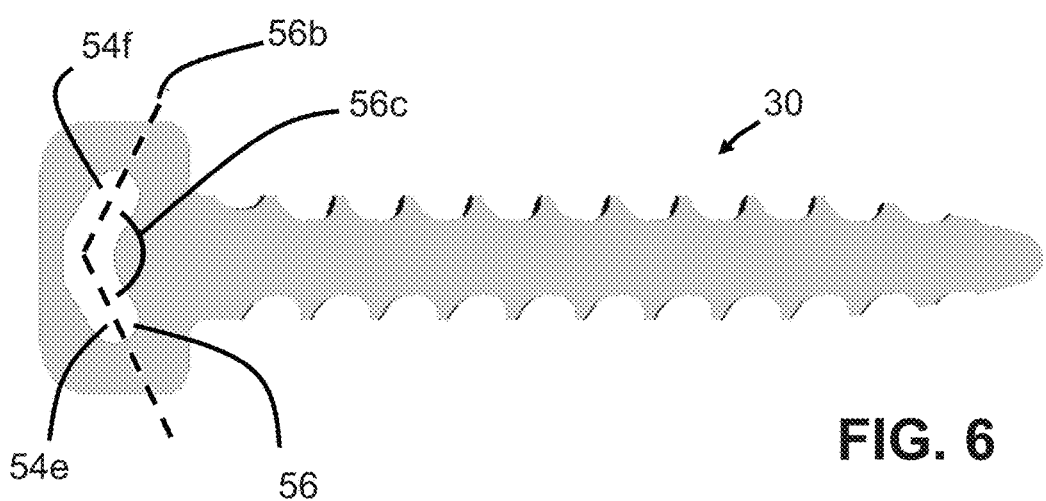
FIG. 6 is a cross sectional representation of the apparatus of FIG. 1 as taken along line 6-6 of FIG. 4.
Figure 7:
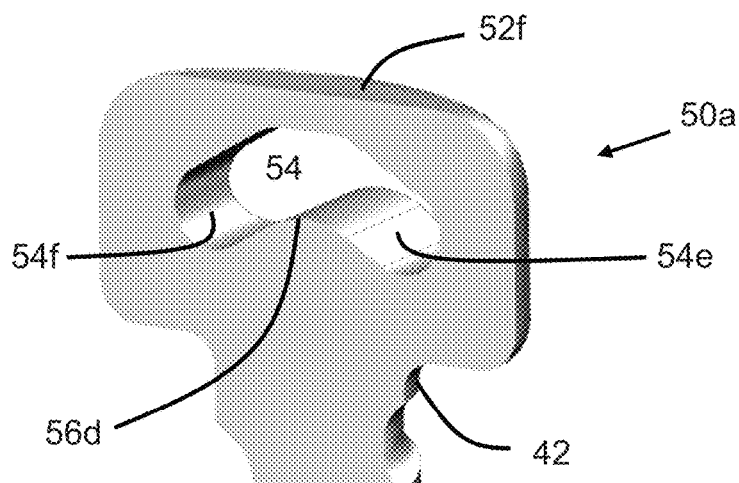
FIG. 7 is a cross sectional, perspective, and enlarged representation of a portion of the apparatus of FIG. 6.
Figure 8:
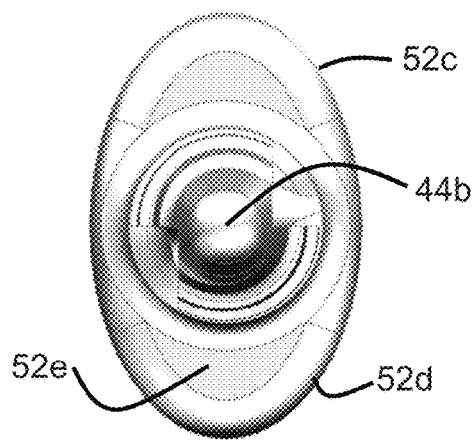
FIG. 8 is a bottom plan view of the apparatus of FIG. 1, looking from the shank toward the head.

Tethering head 50*a* includes within it a passageway 54, as best seen in FIGS. 5, 6, and 7. In some embodiments, this larger passageway 54 includes separated first and second passageways 54*e* and *f*, preferably arranged in a V-shape. Although as shown in FIGS. 6 and 7, the V-shape is "upside down" (with the vertex of the V being proximate to the top surface 52*f* of the head), yet other embodiments include passageways separated in yet other configurations, including V-shapes with the vertex pointed downward, FIG. 8 shapes, barbell shapes, and the like. Still further, yet other embodiments include single passageways of rounded, smooth cross sectional shapes, including circular and elliptical cross sectional shapes, including shapes that are not separated into multiple passageways. Still further, although what has been shown and described includes tethering heads having two passageways, it is further contemplated in yet other embodiments that the tethering heads can include three or more smoothly separated passageways, including separation features having cross sectional shapes resembling a smooth, rounded upside down W-shape.

Figure 9:
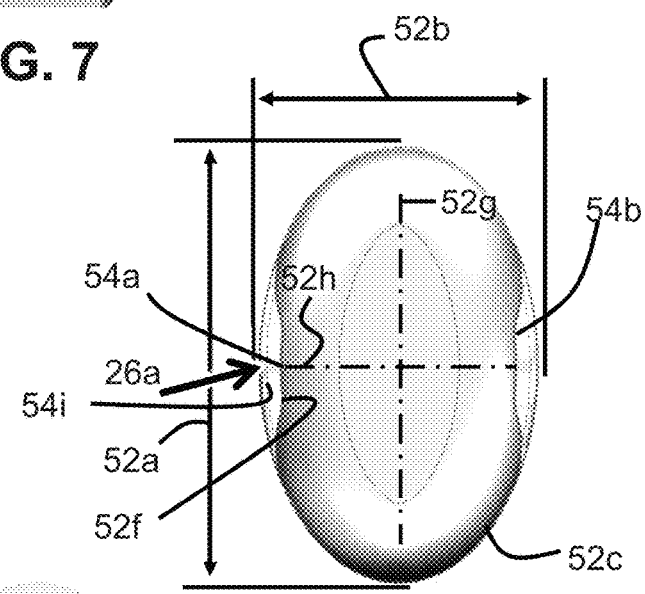
FIG. 9 is a top plan view of the apparatus of FIG. 1, looking from the head toward the shank.

Passageways 54e and 54f are adapted and configured to permit the passage therethrough of the 2 strands of a single continuous (or endless) loop of tethering material. The end of the loop and the strands of the loop are provided to the entrance 54a of the passageways, and leave the passageway through exit 54b (referring to FIG. 9). It is understood that the terms entrance and exit are used for convenience, and that the loop and strands can be entered or exited through either side. Referring to FIG. 9, it can be seen that the shape 52 of head 50 is symmetric about the two planes 52g and 52h as shown. However, other embodiments of the present invention contemplate shapes of tethering heads that have only a single plane of symmetry, or no symmetry at all. In such embodiments, one of the entrance and exit may have one or more distinctly different features than the other of the entrance or exit.

Referring to FIG. 7, in some embodiments the passageways 54f and 54e are separated by a convex feature 56a located on the floor 56 of the passageway. In the embodiment shown, the convex feature 56a is a ridge 56d that extends generally across the width 52b of the head 50a. Referring to FIGS. 6 and 7, this central ridge can be seen to generally follow the upside down V-shape 56b, except with substantially smooth, rounded contours. These smooth and rounded contours of the floor (as well as elsewhere in the various passageways and shapes of the heads X50 shown herein) are useful in minimizing stress concentrations that would otherwise arise in the tethering material, and which could otherwise result in abrasion and potential failure of the tethering material. Although the convex feature 56a of floor 56 is shown as a ridge 56d (in FIG. 7), it is also understood that the convex floor need not extend across the entire width of the passageway, and as another example could be one or more bumps in the floor. It is also understood that other features (such as a convex ceiling of the passageway) could also provide separation of the laterally opposed passageways 54e and 54f.

Referring to FIG. 9, it can be seen that in some embodiments the tethering head 50a has a smooth outer peripheral surface 52d and top surface 52f. In the embodiments shown, the head 52 has an oblong shape, with a maximum width 52a and a central width 52b. As shown in FIG. 9, in some embodiments all peripheral sides of the planform of the head are rounded and smooth so as to minimize abrasion of the tethering loops.

Figure 10:
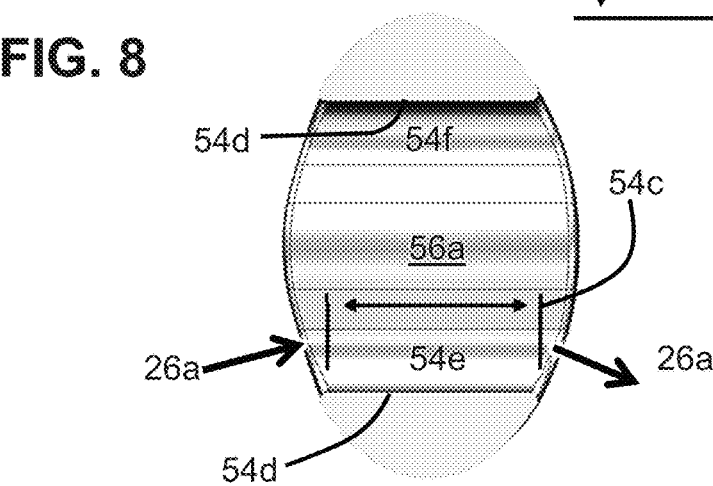
FIG. 10 is a cross sectional view of the apparatus of FIG. 1 as taken along line 10-10 of FIG. 1.
Figure 11:
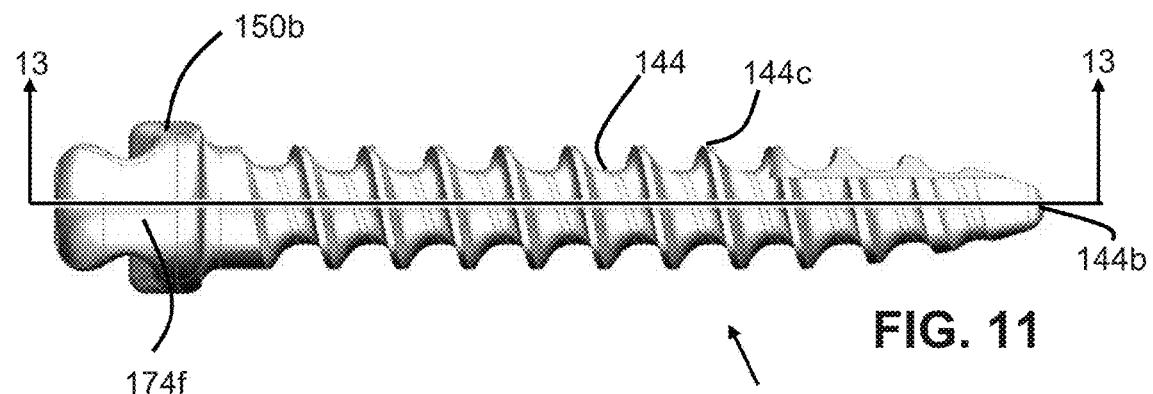
FIG. 11 is a side elevational view of the apparatus of FIG. 2.
Figure 12:
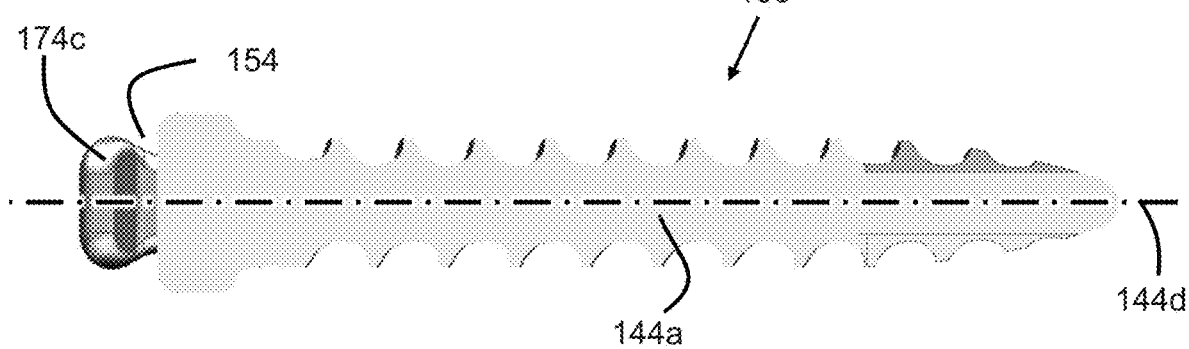
FIG. 12 is a cross sectional representation of the apparatus of FIG. 2 as taken along line 12-12 of FIG. 2.

Comparing FIGS. 9 and 10, it can be seen that the opposing inner walls 54d of the passageway have a width 54c from entrance to exit that is less than the central width 52b of the head shape 52, a result at least in part of the oblong planform shape 52 of the head. In addition, referring to FIG. 9, it can be seen that the top 52f of the head proximate to central plane 52h is slightly relieved inwardly relative to the bottom surface 54i. This slight pullback of the passageway entrance and exit from the edges of the head, combined with the use of an oblong shape in which the passageway cuts through the smaller width of the oblong shape, allows for a wider variation in the approach and departure directions of the loop relative to the passageways.

FIGS. 5, 9 and 10 provide examples of the approach and departure directions of the suture loop relative to head 50a. Preferably, the suture direction 26a is generally through passageway 54, and across the central width 52b. The approach direction 26a shown in FIG. 5 schematically represents this direction, yet the head 50a is adapted and configured such that the approach need not be orthogonal to any particular feature, centerline or symmetry plane of the head. FIG. 9 and FIG. 10 illustrate various approach and departure directions that are acceptable by considering the many smooth, contoured features of the overall head shape, as well as the features previously discussed relative to the entrance and exit of the passageway.

FIGS. 2 and 11-18 show various views of a vertebral tethering member 130 according to another embodiment of the present invention. Tethering member 130 includes a tethering head X50b and means 40 for connecting the head to a vertebrae. Tethering head 150b includes within it an upside down, enclosed V-shaped passageway 154. In the embodiment shown, connecting means 140 is an anchoring screw 44 that includes a plurality of threads 44c on a shaft 44a. Connecting means 40 extends from a neck 42 that attaches to the underside of head 50a to a tip 44b that is adapted and configured to be inserted into a hole in the vertebrae. The necks X42 shown herein preferably include increased cross sectional areas proximate to this attachment, so as to manage the distribution of stresses and forces transitioning between the head and the connection means.

As shown and described herein, means X40 for connecting a head X50 to a vertebrae can be any type of device or method that securely affixes the head X50 to the vertebrae. Examples include the anchoring screws shown in several embodiments herein, as well as a plate, post, hook, clip, or strap, as examples. In the embodiments shown, the connection means 40 includes a neck X42 that provides attachment to the underside 52e of the head 50.

Tethering head 50a includes within it a passageway 54, as best seen in FIGS. 5, 6, and 7. In some embodiments, this larger passageway 54 includes separated first and second passageways 54e and f, preferably arranged in a V-shape. Although as shown in FIGS. 6 and 7, the V-shape is "upside down" (with the vertex of the V being proximate to the top surface 52f of the head), yet other embodiments include passageways separated in yet other configurations, including V-shapes with the vertex pointed downward, FIG. 8 shapes, barbell shapes, and the like. Still further, yet other embodiments include single passageways of rounded, smooth cross sectional shapes, including circular and elliptical cross sectional shapes, including shapes that are not separated into multiple passageways. Still further, although what has been shown and described includes tethering heads having two passageways, it is further contemplated in yet other embodiments that the tethering heads can include three or more smoothly separated passageways, including separation features having cross sectional shapes resembling a smooth, rounded upside down W-shape.

Vertebral tethering member 130 includes a "hitching" or looping-connection head 150b. Comparing FIGS. 13 and 6, it can be seen that the head 150b includes a passageway 154 that looks similar to the passageway 54, except that a slot or opening 73 extends across the top surface 152f. Other similarities between member 130 and member 30 can be seen, such as the passageways 154e and 154f on opposite sides of head 150b, with the passageways being angled in an approximate V-shape 156b, with the included angle 156c of the V-shape being preferably greater than about ninety degrees. Further in comparison of FIGS. 13 and 6, it can be seen that the floor 156 includes a convex feature 156a that roughly parallels the V-shape with a smooth ridge 156d.

One difference between a tethering head X50a and a tethering head X50b is the manner in which the head interfaces with the suture loop. As previously discussed, a tethering head X50a is adapted and configured to guide within it the strands of a tether loop. The tether has an approach direction 26a that in some embodiments has the loop passing through a pair of exits (on lateral sides of the passageway) and a pair of exits (also on corresponding lateral sides of the passageway).

Figure 13:
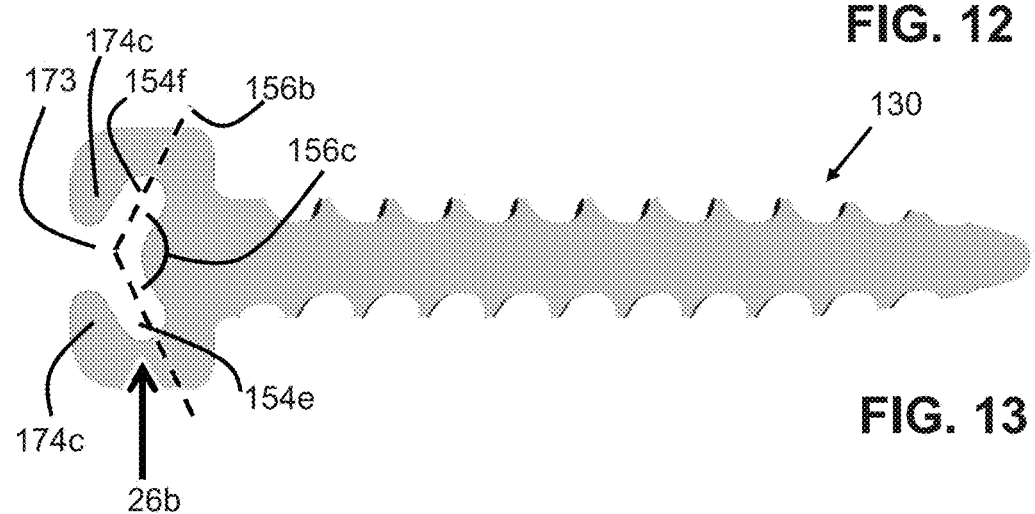
FIG. 13 is a cross sectional representation of the apparatus of FIG. 1 as taken along line 13-13 of FIG. 11.

In comparison, a tethering head X50b in some embodiments contemplates a suture loop approaching direction 26b (referring briefly to FIGS. 15 and 17) that is generally orthogonal to the approach direction 26a. As best seen in comparing FIGS. 14 and 16 to FIGS. 7 and 9, respectively, is that a tethering head X50b is adapted and configured to be loopingly connected (or hitched) to a post X74 of the head X50b. Referring briefly to FIGS. 13 and 17, it can be seen that the suture approach direction 26b is in a direction generally orthogonal to the approach direction 26a for a head 50a, as seen in FIGS. 5 and 10.

Yet another difference between a tethering head X50a and a tethering head X50b is the placement of a slot 173 that extends through the top surface 152f of a head X50b. This slot 173 preferably has a width 173a and also smoothing and contouring features that adapt it and configure it to permit downward passage of a loop of suture. Referring to FIG. 14 and FIG. 18, it can be seen that the slot, combined with preferably significantly radiused edges 174b proximate to a minimum cross sectional area 174d, in combination with passageways 154e and 154f, create first and second suture loop hitching posts 174f and 174g.

A tethering head X50b according to various embodiments of the invention is attached to an undercut location along either of two laterally facing posts 174f or 174g. Comparing FIGS. 13 and 17, it can be seen that the suture loop approach direction 26b does not have to be at a right angle (as suggested by FIG. 13) but can be at any angle (as shown in FIG. 17) that still permits the loop to be protectively retained under the overhang 174c of the attachment post 174.

FIG. 17 shows additional features that permit a variety of approach directions toward the hitching post 174. As one example, it can be seen that the width of the passageway 154c is shorter than the maximum width 174a of the post (as shown toward the bottom of FIG. 17). A radiused edge 174b transitions from width 154c of the inner wall 154d to the maximum width 174d. This radius 174b is adapted and configured to eliminate or minimize any stress concentration in the suture loop as it wraps around the corner 174b. FIG. 17 also shows that the angular extent 174e defined between the tangent lines 174h is in excess of ninety degrees. Comparing FIGS. 15 and 17, it can be seen that the radiused corners 174b and angular extent 174e of the entrance or exit permits a variety of suture approach directions that can differ significantly from the plane 152g that includes the major axis of the oblong head.

These various contouring features described above, along with the slot 173 and V-shape 156b, also combine to create an overhanging portion 174c for each post. This overhanging portion 174c (best seen in FIGS. 13 and 18) extends from the respective post in a direction generally opposite to the direction of tension that would be applied to the suture loop. Because of this overhang, any attempt at vertical movement of the suture loop is discouraged, since any movement of the suture loop away from the minimal cross sectional area 174d and toward the overhand 174c would require increased tension in the loop, and thus resist the attempted vertical movement. Therefore, the placement of the minimum cross sectional area between the overhand 174c and the floor convex feature 158 discourages top to bottom movement of the loop, and encourages placement of the loop around the minimum cross sectional area.

FIGS. 3 and 19-22 show various views of a vertebral tethering member 230 according to another embodiment of the present invention. Tethering member 230 includes a tethering head X50c and means 40 for connecting the head to a vertebrae. Tethering head 250c includes within it an upside down, enclosed V-shaped passageway 254. In the embodiment shown, connecting means 240 is an anchoring screw 44 that includes a plurality of threads 44c on a shaft 44a. Connecting means 40 extends from a neck 42 that attaches to the underside of head 50a to a tip 44b that is adapted and configured to be inserted into a hole in the vertebrae. The necks X42 shown herein preferably include increased cross sectional areas proximate to this attachment, so as to manage the distribution of stresses and forces transitioning between the head and the connection means.

As shown and described herein, means X40 for connecting a head X50 to a vertebrae can be any type of device or method that securely affixes the head X50 to the vertebrae. Examples include the anchoring screws shown in several embodiments herein, as well as a plate, post, hook, clip, or strap, as examples. In the embodiments shown, the connection means 40 includes a neck X42 that provides attachment to the underside 52e of the head 50.

Tethering head 50a includes within it a passageway 54, as best seen in FIGS. 5, 6, and 7. In some embodiments, this larger passageway 54 includes separated first and second passageways 54e and f, preferably arranged in a V-shape. Although as shown in FIGS. 6 and 7, the V-shape is "upside down" (with the vertex of the V being proximate to the top surface 52f of the head), yet other embodiments include passageways separated in yet other configurations, including V-shapes with the vertex pointed downward, FIG. 8 shapes, barbell shapes, and the like. Still further, yet other embodiments include single passageways of rounded, smooth cross sectional shapes, including circular and elliptical cross sectional shapes, including shapes that are not separated into multiple passageways. Still further, although what has been shown and described includes tethering heads having two passageways, it is further contemplated in yet other embodiments that the tethering heads can include three or more smoothly separated passageways, including separation features having cross sectional shapes resembling a smooth, rounded upside down W-shape.

Figure 19:
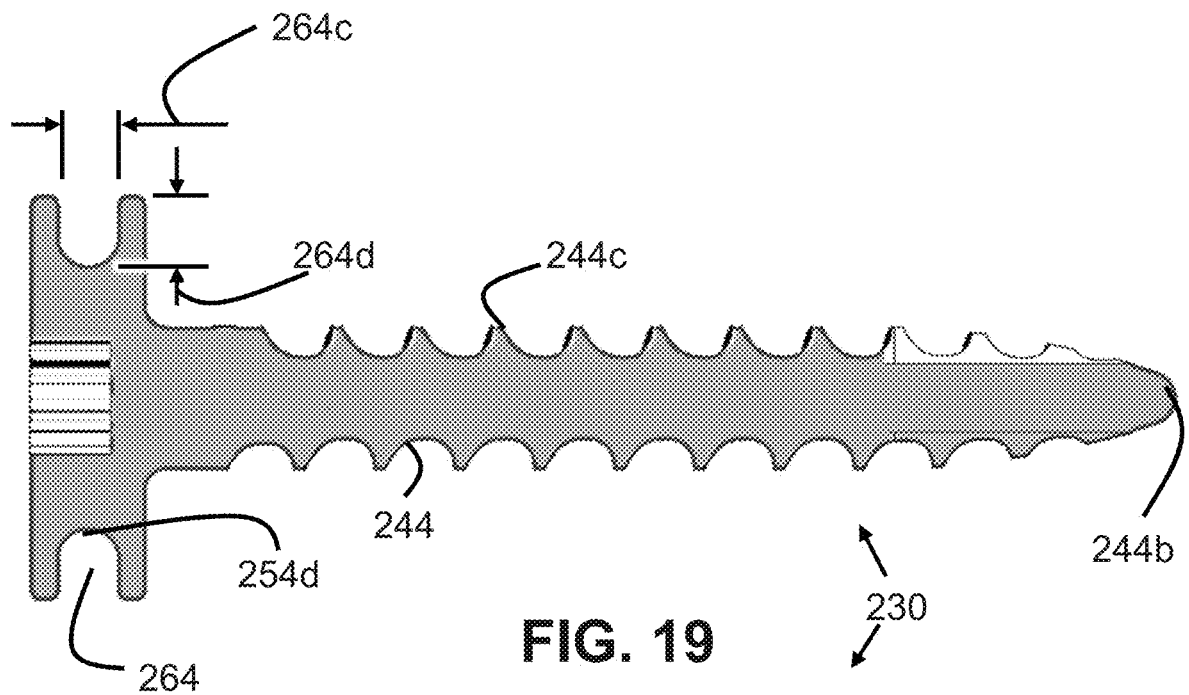
FIG. 19 is a cross sectional representation of the apparatus of FIG. 3 as taken along line 19-19.
Figure 20:
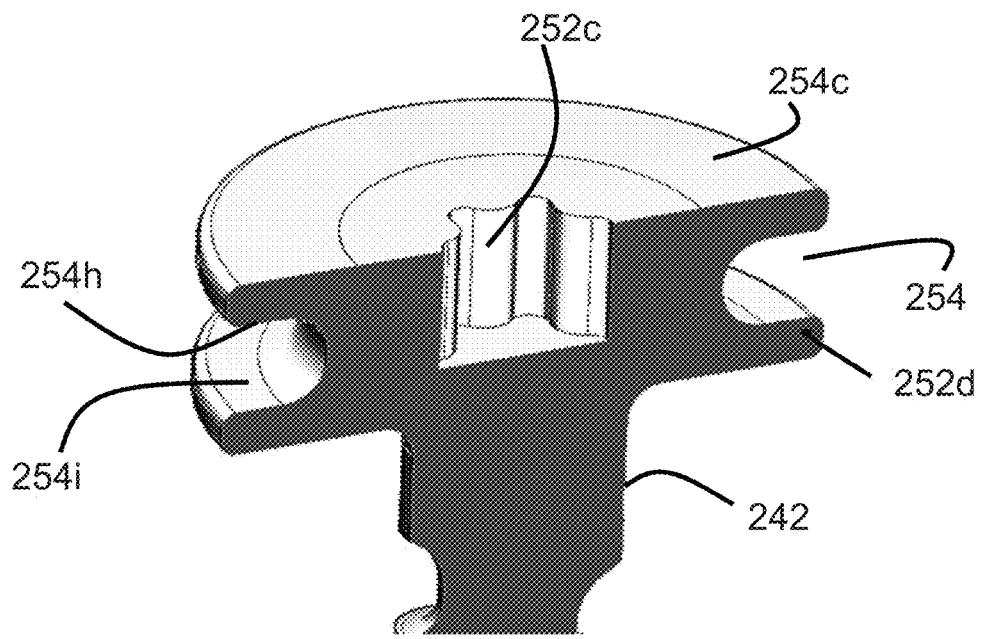
FIG. 20 is a perspective view of a portion of the apparatus of FIG. 19.

Vertebral tethering member 230 includes a tethering head 250c adapted and configured for looping connection to a flexible tether or suture. Referring to FIG. 19, it can be seen that a tethering head X50c preferably includes a peripheral groove 264 that extends around the smooth outer surface 252d of head 250c. In one embodiment, this groove is recessed into the periphery, with the inner wall 254d of the groove being smoothly contoured and rounded for minimal abrasion with a suture loop placed within the groove. In one embodiment, as shown in FIG. 19, the inner wall 254d has a semi-circular shape, although other embodiments of the present invention contemplate smoothly contoured and rounded walls of any shape, including walls having elliptical cross sections and parabolic cross sections as examples.

Preferably, the groove includes a top and bottom pair of walls 254h and 254i, respectively that, combined with the innermost wall 254d, form the suture loop passageway 254. Preferably, this passageway has a width 264c greater than the unstressed diameter of the suture material, as well as a depth 264d greater than the unstressed diameter of the suture material. By having groove dimensions greater than the unstressed diameter, the physician will easily wrap the unstressed loop around and into passageway 254, and preferably without the need to push or force the suture material into the groove. However, yet other embodiments of the present invention contemplate a groove 264c in which the unstressed material fits tightly and securely within the groove.

In a manner similar to the post overhangs 174c previously discussed, the top and bottom surfaces 254h and 254i, combined with the depth 264d of passageway 254, result in the implanted suture remaining securely within the groove, and not escaping the groove even if the tension on the suture is slightly relieved. The overhang of the top and bottom walls 254h and 254i also provide protection to the suture loop within groove 254 from abrasion from other nearby features.

Figure 21:
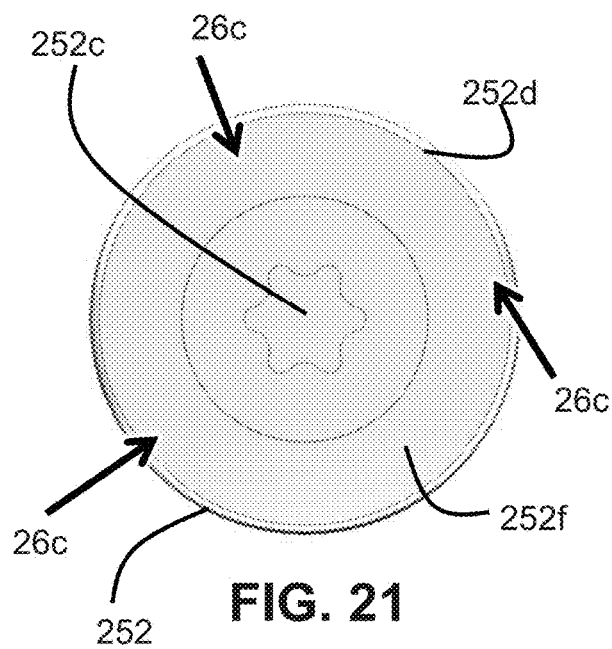
FIG. 21 is a top plan view of the apparatus of FIG. 3 of the head looking toward the shaft.

It is noted that the suture placed within groove 264 should be large enough to fit over the peripheral shape 252 of the head 250c, as best seen in FIG. 21. Comparing head 250c and 150b (shown in FIG. 16), it can be seen that the loop of suture material for head X50b should be large enough to fit over the top surface 152f of a post 174.

Figure 23:
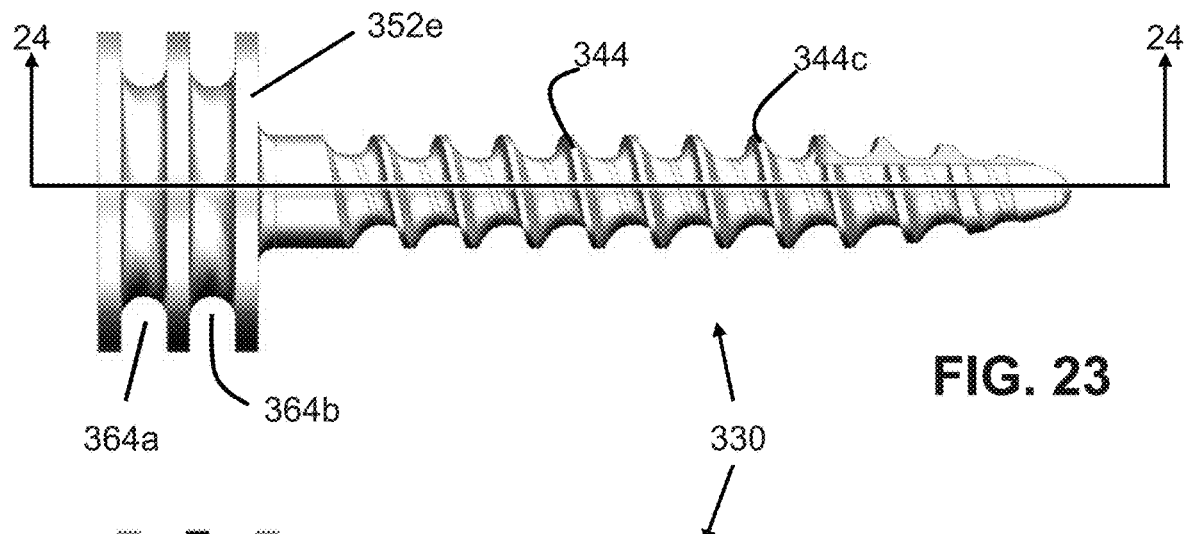
FIG. 23 is a CAD surface representation of a vertebral tethering member according to yet another embodiment of the present invention.
Figure 24:
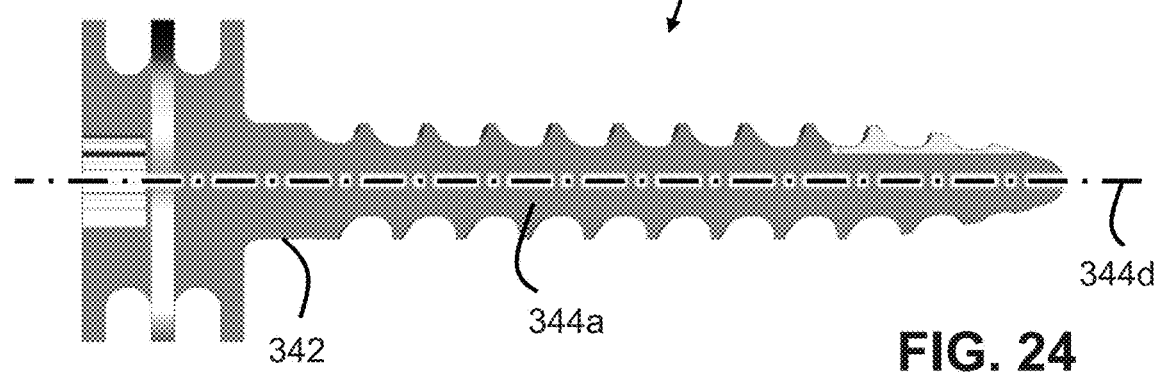
FIG. 24 is a cross sectional view of the apparatus of FIG. 23 as taken along line 24-24 of FIG. 23.
Figure 25:
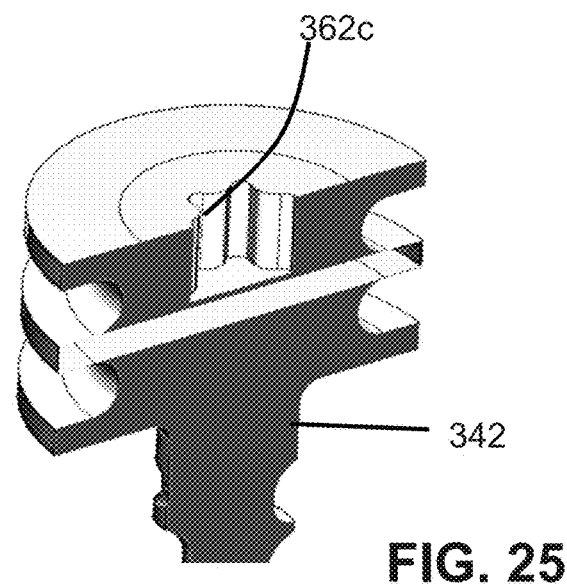
FIG. 25 is a perspective, enlarged view of a portion of the apparatus of FIG. 24.

FIGS. 23, 24, and 25 depict various aspects of a vertebral tethering member 330 similar to the member 230 previously discussed. Member 330 is similar to member 230, except including a pair of spaced apart peripheral grooves 364a and 364b. Preferably, these grooves are spaced apart vertically from the underside, bone contacting surface 352e. Member 330 permits a single tethering member to apply tension in two different directions, each direction being provided by a different suture loop.

Figure 26:
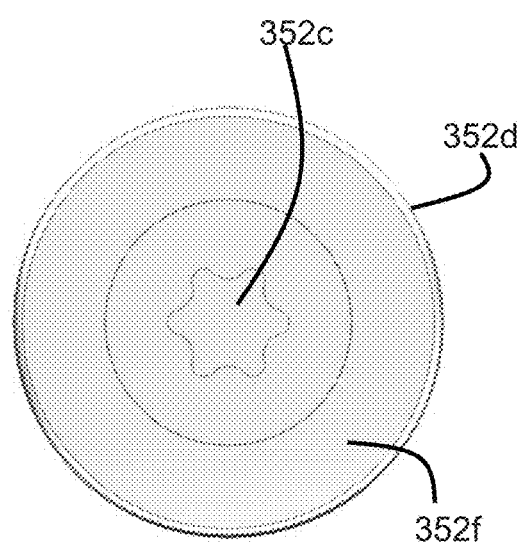
FIG. 26 is a top plan view of the apparatus of FIG. 23 from the head looking toward the shaft.
Figure 22:
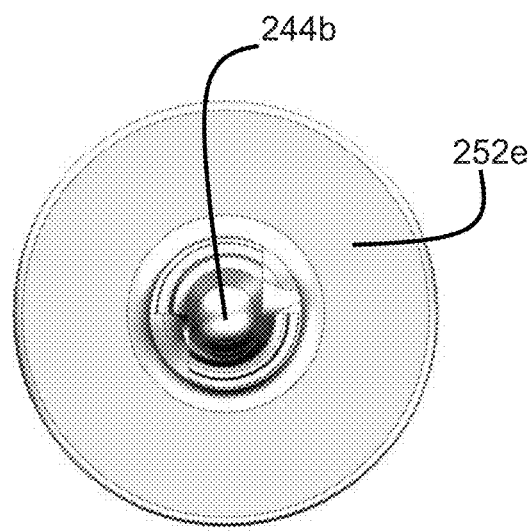
FIG. 22 is a bottom plan view of the apparatus of FIG. 3 of the shaft looking toward the head.
Figure 27:
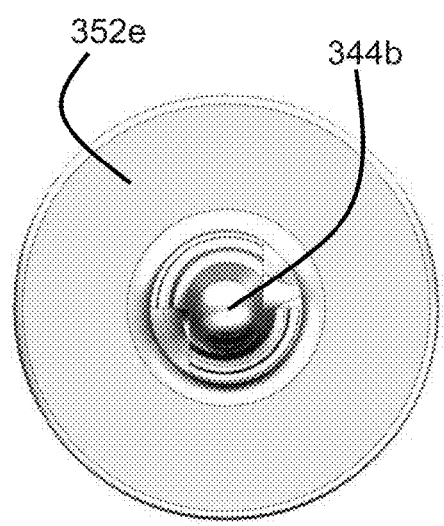
FIG. 27 is a bottom plan view of the apparatus of FIG. 23 from the shaft looking toward the head.

FIGS. 21 and 22 show top and bottom views, respectively, of tethering member 230. FIGS. 26 and 27 show similar top and bottom views, respectively, of tethering member 330. Each tethering member includes a central driving feature 252c for applying torque to the tethering member. Further, both tethering members permit a variety of suture approach directions 26c, as shown with FIG. 21. The strands of the suture can exit radially outwardly in any direction. Still further, a strand (and not a complete loop) can be wrapped part way around the groove, and depart (or approach) a head X50c tangentially to the groove, as expressed by the arrow 26c of FIG. 21 shown at about the three o'clock position. It is understood that the tethering member 330, as discussed above, is adapted and configured to provide connection to two different suture loops, each approaching in two different directions, and in any of the manners discussed with regard to tether member 230.

FIGS. 28-30 show various views of a vertebral tethering member 430 according to one embodiment of the present invention. Tethering member 430 includes a tethering head 50a and means 40 for connecting the head to a vertebrae. Tethering head 50a includes within it two enclosed, separated passageways 454.

In the embodiment shown, connecting means 440 is a plate adapted and configured to be attached by a plurality of vertebral anchors (not shown) to a vertebrae. Connecting means 440 has a generally rectangular planform shape and includes a plurality of through holes 446a adapted and configured for securement of the plate 446 to the vertebrae by the connecting means. Although what is shown and described is a rectangular plate having four evenly spaced holes for fasteners, it is understood that the shape of plate 446 can be of any type adapted and configured for attachment to a vertebrae.

Tethering member 430 includes a guiding head X50a adapted and configured for providing passage therethrough of a suture loop. Head 450a includes a pair of spaced apart passageways 454f and 454e separated completely by a ridge 456d. Referring to FIGS. 28, 30 and 31, it can be seen that the entrance and exit of the passageways are rounded and smoothly contoured to permit a variety of suture approach directions 26a, with minimal or no abrasion to the suture loop.

In some embodiments, each passageway 454e or 454f can provide guidance therethrough for both strands of a suture loop. In yet other embodiments, the individual strands of the suture loop are separated, with one strand passing through each of the passageways. In still further embodiments, it is understood that a single passageway 454e or 454f can be sized and adapted and configured to permit passage therethrough of multiple loops, single strands of different loops, or combinations thereof.

FIGS. 32, 33, and 34 depict yet further embodiments of the present invention, each including in the example shown a plate X46 for attachment of the tethering head to the vertebrae. FIG. 32 is a side elevational view of a tethering member 530 which is similar to tethering head 430 as shown and discussed. However, each of the passageways 554e and 554f include respective slots 573 that permit a suture loop to be passed into the corresponding passageway.

FIG. 33 shows a side elevational view of a vertebral tethering member 630 according to another embodiment of the present invention. Tethering member 630 is similar to tethering member 430 previously shown and discussed. However, tethering head 630 includes a convex feature 656a extending generally from a first surface 646c of plate 646, but not extending completely to the top wall 654h of head 650a. The cross sectional shape of head 650a as shown in FIG. 33 is similar in function to the fastener head 50a previously shown and discussed with regards to tethering member 30. However, it is appreciated that the cross sectional shape of the passageways is more of a figure-8 or barbell shape.

FIG. 34 shows a side elevational view of a tethering member 730 according to another embodiment of the present invention. Tethering member 730 includes connection means 740 comprising a plate 746 similar to that shown and discussed with regards to embodiment 430. However, member 730 includes a hitching-type tethering head 750b having function similar to that of anchor 130 previously discussed. Head 750b is adapted and configured to provide a pair of spaced apart posts 774f and 774g having function similar to the aforementioned hitching post.

FIGS. 35-39 depict the implantation and usage of the vertebral tethering members X30 described herein. As will be shown and discussed, various combinations of different tethering members X30 can be attached to adjacent vertebrae, or to the same vertebrae. A plurality of the tethering members X30 can be interconnected to one or several other tethering members X30. Further, these tethering interconnections can be accomplished with one or multiple loops of suturing or tethering material.

Figure 35:
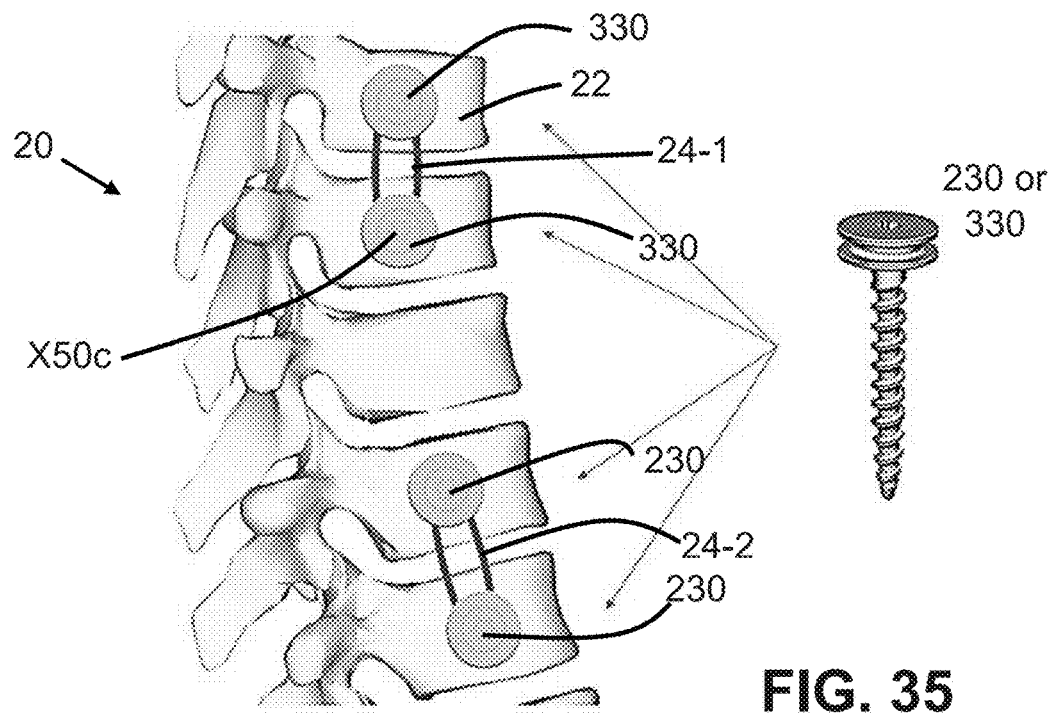
FIG. 35 is a schematic representation of an arrangement of vertebral tethering members and sutures according to another embodiment of the present invention, and showing two level constructs.

FIG. 35 shows a plurality of looping connection tethering members 230 and/or 330. In the top portion of FIG. 35, a pair of tethering members 330 are shown coupled to adjacent vertebrae 22 of a spine 20. A single suture loop 24-1 is shown interconnecting the two tethering heads X50c. At the bottom of FIG. 35, a second, separate tethering loop 24-2 is shown looped around the peripheral grooves 264 of vertebral tethering members 230, each secured to different vertebrae.

Figure 36:
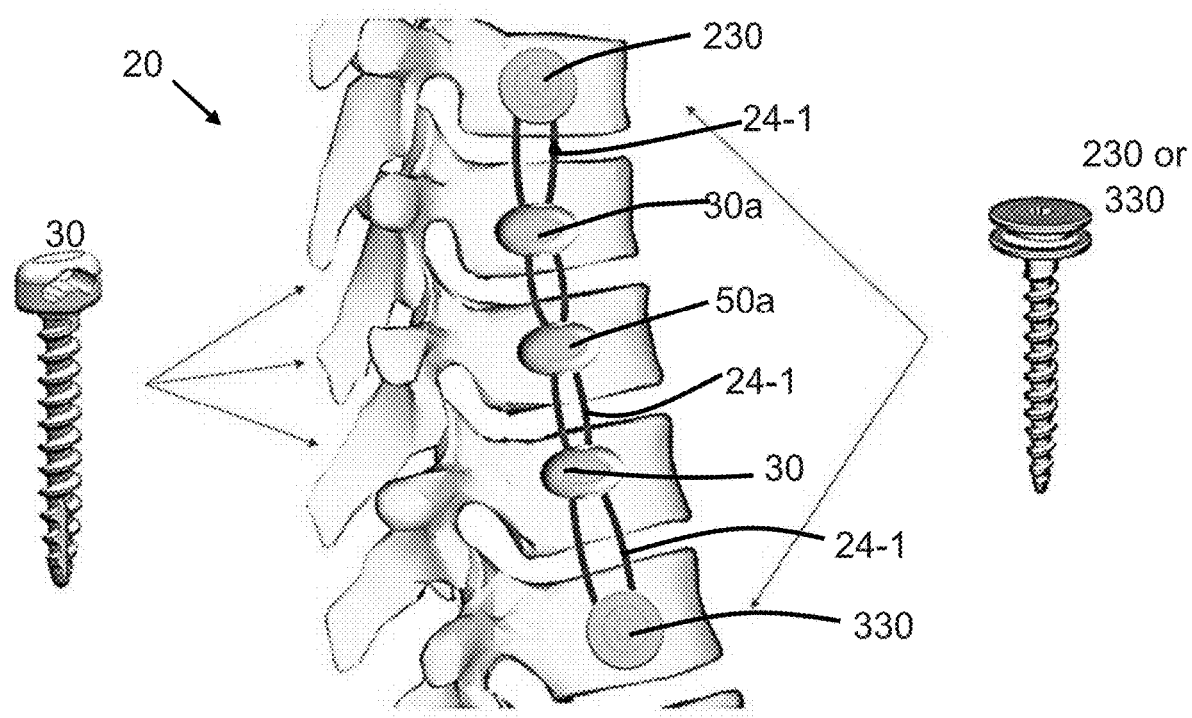
FIG. 36 is a schematic representation of an arrangement of vertebral tethering members and sutures according to another embodiment of the present invention, and showing multiple level constructs, with a single loop tensioned across end points.

FIG. 36 shows a single tethering loop 24-1 extending from a topmost tethering member 230 to a bottommost tethering member 330. The single tethering loop passes through three tethering members 30a, each having a tethering head 50a that provides guidance for the passage therethrough of the single suture loop.

Figure 37:
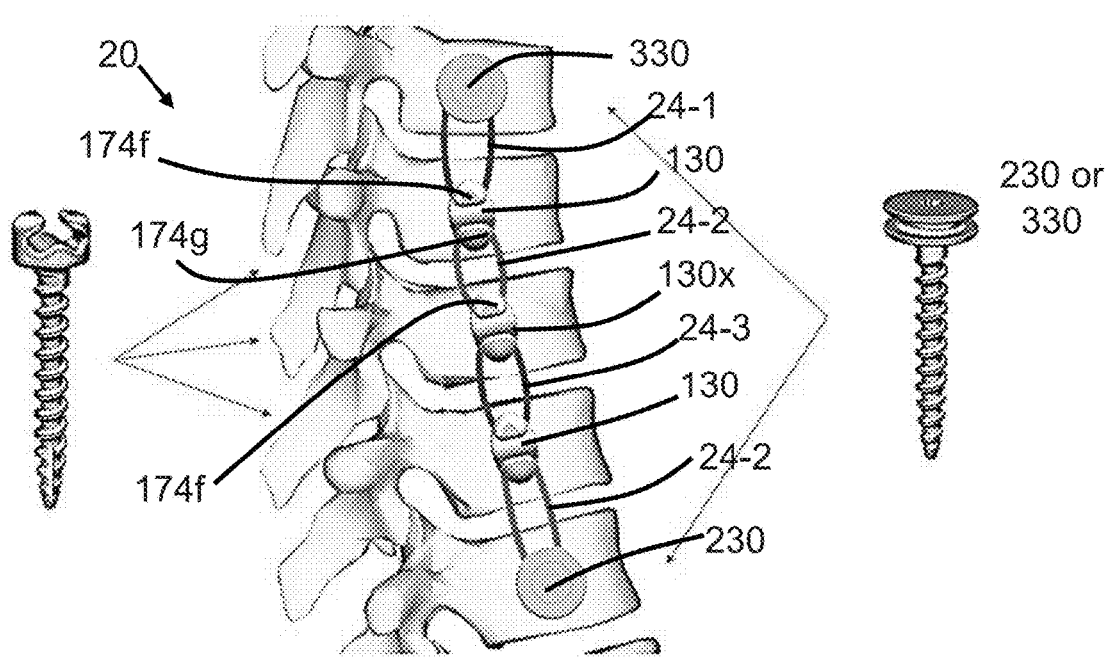
FIG. 37 is a schematic representation of an arrangement of vertebral tethering members and sutures according to another embodiment of the present invention, and showing multiple level constructs, with each loop tensioned independently.

Referring to FIG. 37, a spine 20 has implanted within it a plurality of tethering members X30, each of which is interconnected by separate tethers to adjacent tethering members. A first suture loop 24-1 passes around the peripheral groove 364 of a member 330, and then to a first post 174f of the member 130 attached to the adjacent vertebrae. A second suturing loop 24-2 interconnects the other securement post 174g to a tethering post 174f secured to an adjacent vertebrae. This pattern continues through several adjacent vertebrae.

It is further understood that the present invention also contemplates combining in one implantation a mixture of looping members 230 or 330, with both guiding members 30 as well as hitching members 130. For example, in the implantation constructions shown in FIG. 34, the central-most hitching member 130x could be replaced with a guiding member 30x, such that the loop 24-2 extends through the guiding member 130, and is then linked to a post of the next adjacent hitching member 130. In such a construction, the vertebrae to which guiding member 30x is attached would be somewhat freer to establish its own position between the adjacent vertebrae.

Figure 38:
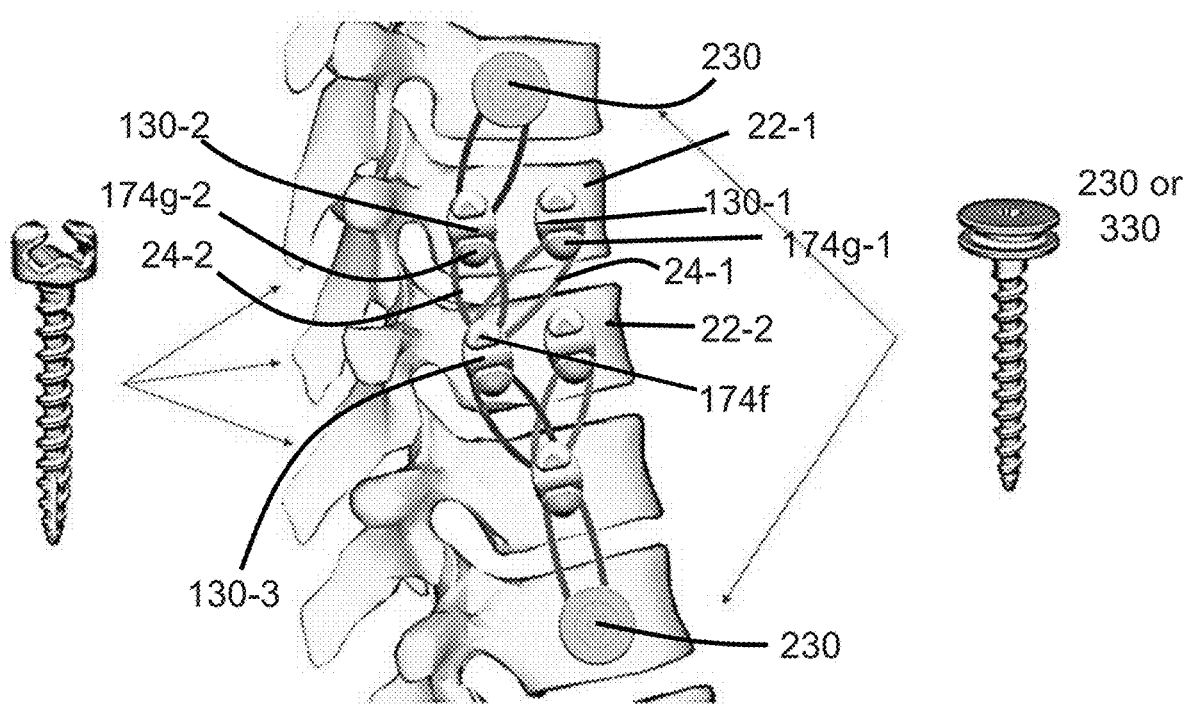
FIG. 38 is a schematic representation of an arrangement of vertebral tethering members and sutures according to another embodiment of the present invention, showing the use of multiple anchors for derotation.
Figure 39:
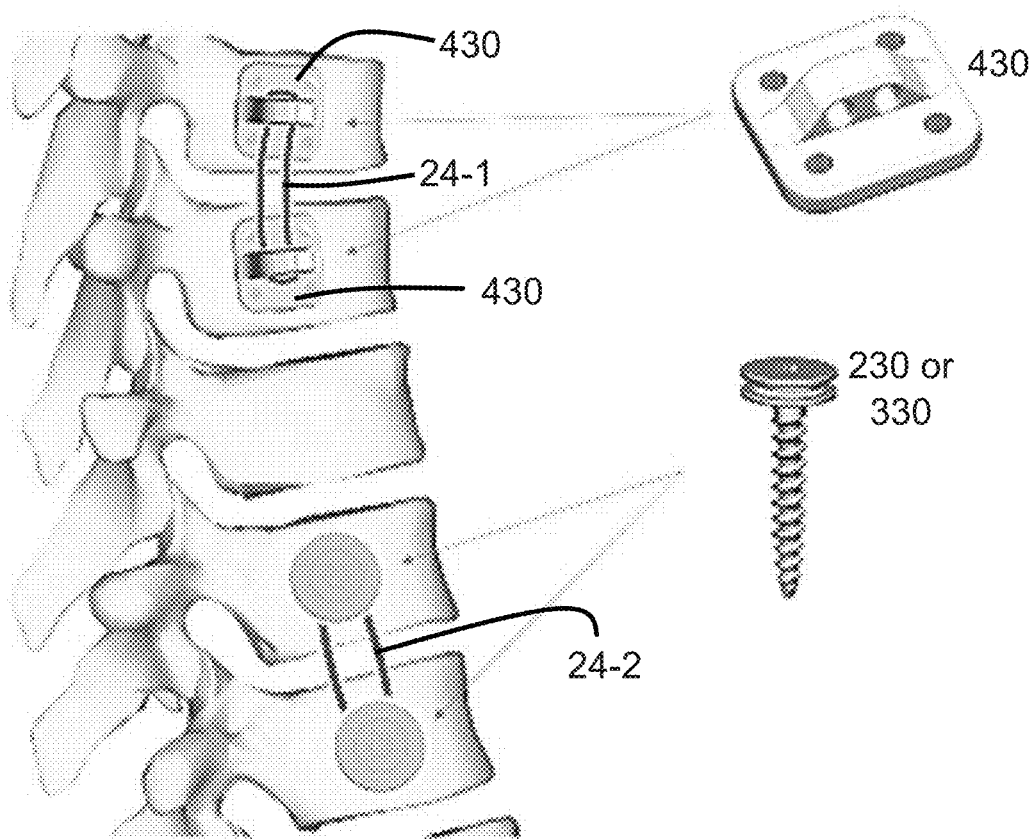
FIG. 39 is a schematic representation of an arrangement of vertebral tethering members and sutures according to another embodiment of the present invention.

Referring to FIG. 38, a pair of vertebral tethering members 130-1 and 130-2 have been secured to a single vertebrae. A third tethering member 130-3 has been secured to an adjacent vertebrae. A common securement post 174f is connected by two suture loops 24-1 and 24-2 to the suturing post 174g-1 and 174g-2 of corresponding members 130-1 and 130-2. In this manner, the lateral offset between members 130-2 and 130-1 can apply a rotational torque of vertebrae 22-1 relative to vertebrae 22-2.

FIGS. 40-48 depict a vertebral tethering member 830 according to another embodiment of the present invention. Tethering member 830 includes a tethering head 850a that is adapted and configured to provide guidance of a flexible connection 24 (not shown).

Tethering member 830 includes means 840 for connecting tethering head 850a to a vertebrae or other bone. In one embodiment, and referring to FIG. 43, it can be seen that tethering member 830 includes anchoring means 840 that is separable from head 850a. Guiding head 850a further comprises at least two separable components, comprising a receiving head 880 that receives within it at least one tethering member or connection receiver 890. As will be shown and discussed further, in a preferred embodiment tethering member 830 includes two flexible connection receivers 890, and in such embodiments tethering member 830 comprises four separable components (bone connecting means 840, receiving head 880, and first and second tethering members 890). However, it is understood that the invention further contemplates assemblies having a single flexible connection receiver 890, or any plurality of connection receivers.

Referring to FIGS. 43, 44, and 45, it can be seen that the one or more flexible connection receivers 890 include a body 898 having at least one protrusion 896b, preferably extending laterally and outwardly from the body. In some embodiments, protrusion 896b includes a single passageway 896a extending through the projections, and providing a smooth, non-abrasive pathway for a flexible connection, such as a suture, cord, cable, or tether. However, still other embodiments contemplate multiple thru-passageways 896a, such that multiple tethers can be attached to the same projection. As shown in tethering member 830, the passageway 896a is oriented to be generally perpendicular of the central axis 844d of the anchor 844. However, still other embodiments contemplate passageways 896a oriented generally parallel to axis 844d, or in any orientation relative to axis 844d, including orientations that are non-tangential to the circular outer shape of member 830 (this preferred tangential orientation best seen in FIGS. 47 and 48).

Preferably, tethering head assembly 850a is modular in design. As shown in FIG. 43, this assembly includes a receiving and alignment head 880 having a central pocket 882b that is adapted and configured to receive within it one or more separable flexible connection receivers 890. The central pocket 882b of receiving head 880 has an internal shape 882c defined by sidewalls 882a and sidewall apertures 884a. The tethering receiving member 890 comprises a body 898 having an outer shape 894 that in some embodiments is generally complementary to, and a close fit within, the internal shape 882c of pocket 882b. In yet other embodiments, the shape of the protrusion 896b is adapted and configured to preferably fit closely within sidewall apertures 884a. However, the present invention also contemplates those embodiments in which only one of the outer shape 894 or the protrusion 896b is a close fit in the corresponding feature of the receiving head 880, and also those embodiments in which neither provide a close fit.

As would be understood by those of ordinary skill in the art, and with reference to FIGS. 43 and 44, it can be seen that the arrangement of bone connecting member 840 and tethering head 850a can be accomplished with satisfactory securement of the four separable pieces in various ways. As one example, the close fit may be provided by the outer diameter 842 with the inner diameter of the separable receivers 890, in which case in some embodiments the outer diameter of the receivers will be a looser fit within the sidewalls 882a of pocket 882b. Oppositely, it is contemplated in some embodiments that the closer and tighter fit between the separable receivers 890 be accomplished between their outer diameters and the inner diameter of sidewalls 882a, with the clearance between the outer diameter 842a and inner diameter of the apertures 892 being a looser fit.

Referring to FIGS. 44 and 45, it can be seen that in some embodiments the neck 842 of connecting means 840 provides a radial alignment function to the various separable components of guiding head 850a. In one embodiment, the neck 842 has a generally circular shape that fits within the central aperture 892 of each tethering member 890, and further within the central aperture 886 of receiving head 880. In some embodiments, this alignment and fitment provided by neck 842 is of a relatively close fit, and in some embodiments permits limited rotation of the aligned and captured tethering member 890, at least within the looseness of the protrusion 896b within sidewall aperture 884a. In still other embodiments, the axial alignment is not a close fit.

In still further embodiments, the neck 842 of connecting means 840 provides no interface with the separable ring 890, but does include one or more aligning elements preferably on both the top portion 841 and the receiving head 880. In one embodiment as shown in FIG. 44, the interface between top portion 841 and receiving head 880 is an abutment of surfaces in compression after coupling of the threads to a bone. However, in yet other embodiments the top portion 841 could include threads for threaded coupling to receiving head 880, which threaded interface could be at the top of the sidewalls 882*a*, or could be within the central aperture 886. In some such embodiments, the connection between the tethering apparatus and the bone can be by way of a plate X46, in which the assembly of top portion, at least one separable receiver, and receiving head is attached to a plate, and the plate is coupled such as by way of fasteners or other to a bone.

Figures 46, 47, 48:
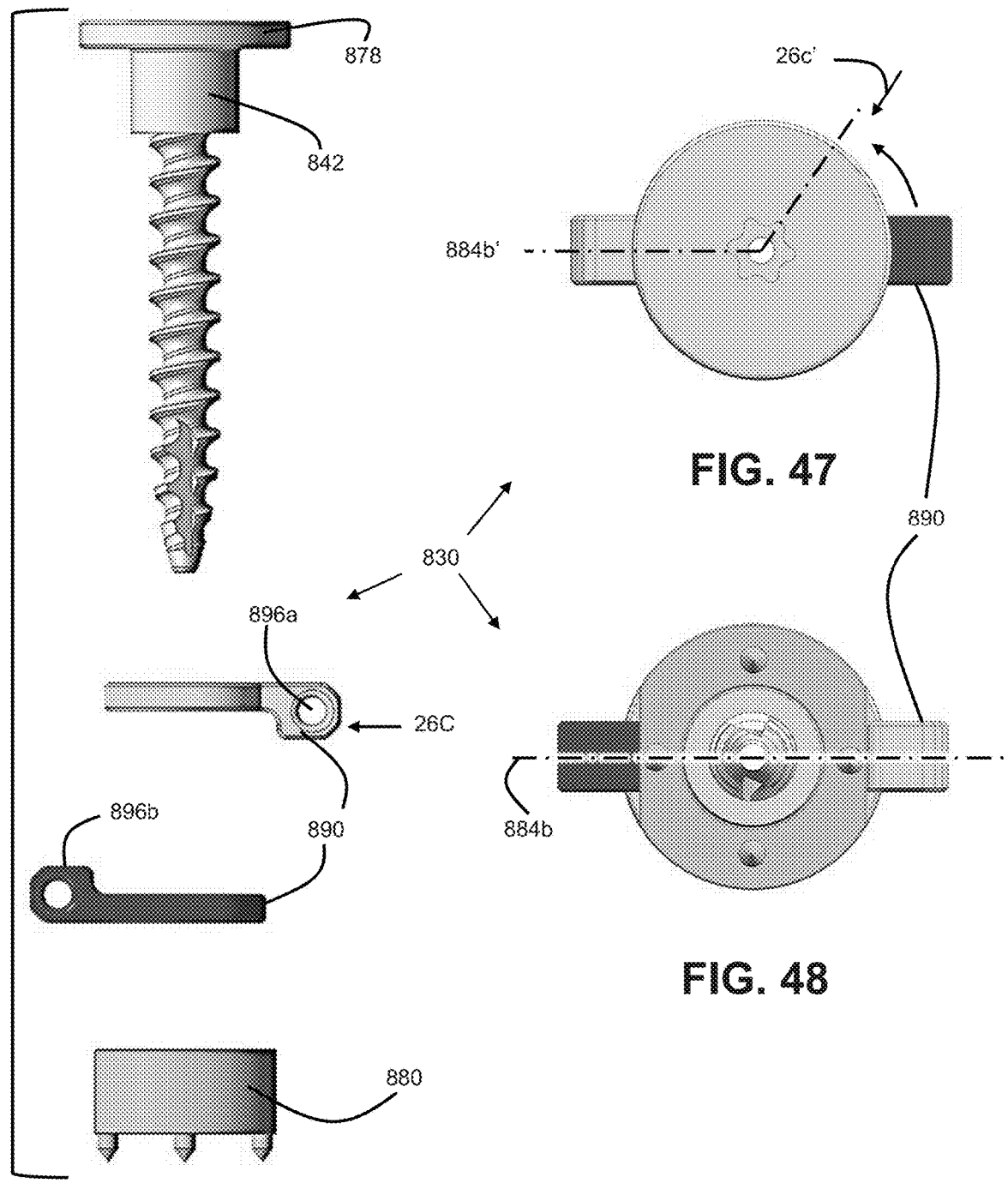
FIG. 46 is a side elevational exploded view of the apparatus of FIG. 41.
FIG. 47 is a top plan view of the apparatus of FIG. 41 as taken along line 47-47.
FIG. 48 is a bottom plan view of the apparatus of FIG. 41 as taken along line 48-48.

Referring to FIGS. 43 and 48, it can be seen that the sidewall apertures 884*a* of receiving and alignment head 880 are preferably angularly displaced by one hundred and eighty degrees, and generally aligned oppositely along a laterally extending axis 884*b*. However, in still other embodiments, the apertures can be angularly displaced by less than one hundred and eighty degrees, as it noted by alignment axis 884*b*', as shown on FIG. 47. Those of ordinary skill in the art can further recognize from FIG. 47 the possibility of having a multiple sidewall apertures, whether evenly spaced angularly or not.

Various aspects of different embodiments of the present invention are expressed in paragraphs X1, X2, X3, X4, X5, X6, X7 and X8 as follows:

X1. One aspect of the present invention pertains to a member for connection to a bone. The member preferably includes a head and means for connecting the head to a vertebra. The member preferably includes means for coupling the head to a flexible material.

X2. Another aspect of the present invention pertains to a member for tethered connection to a bone. The member preferably includes a bone connecting member adapted and configured for connection with a vertebra. The member preferably includes a head attached to the bone connecting member, the head at least one passageway extending across the head; the passageway being adapted and configured to accept therein a corresponding tether, the passageway having an entrance on one side of the head and an exit on the opposing side of the head, the passageway being enclosed from the top surface of the head.

X3. Yet another aspect of the present invention pertains to a member for tethered connection to a bone. The member preferably includes a bone connecting member adapted and configured for connection with a vertebra. The member preferably includes a head attached to the bone connecting member, the head including at least one securement post each adapted and configured for connection to a loop of a flexible tether, the post including a groove sized to accept therein a tether loop.

X4. Still another aspect of the present invention pertains to a member for tethered connection to a bone. The member preferably includes a bone connecting member adapted and configured for connection with a vertebra. The member preferably includes a head attached to the bone connecting member, the head including at least one peripheral groove adapted and configured for connection to a separate loop of flexible tether, the head having a top surface furthest away from the vertebrae, wherein the at least one peripheral groove is between the top surface and the vertebra.

X5. Another aspect of the present invention pertains to a method for tethering of vertebrae. The method preferably includes attaching a first tethering head to a first vertebra. The method preferably includes attaching a second tethering head to the first vertebra spaced apart from the first tethering head. The method preferably includes attaching a third tethering head to a second vertebra. The method preferably includes looping one end of a first flexible tether in a first groove in the first tethering head. The method preferably includes looping one end of a second flexible tether in a second groove in the second tethering head. The method preferably includes connecting the first vertebra to the second vertebra by looping the other end of the first flexible tether within a groove in the third tethering head, and connecting the first vertebra to the second vertebra by looping the other end of the second flexible tether within a groove in the third tethering head.

X6. Yet another aspect of the present invention pertains to a method for tethering of vertebrae. The method preferably includes attaching a first tethering head to a first vertebra. The method preferably includes attaching a second tethering head to a second vertebra. The method preferably includes looping a flexible tether in a first groove extending around the periphery of the first tethering head. The method preferably pertains to extending the looped tether from the first tethering head to the second tethering head; and passing the extension of the looped tether though an aperture in the second tethering head.

X7. Still another aspect of the present invention pertains to a device for making a flexible connection between bones. The device preferably includes a bone connecting member adapted and configured for connection with a vertebra, the bone connecting member including an alignment feature. The device preferably includes a separable receiver for a flexible connector, the receiver having a body including a protrusion with a passageway for a flexible connector and including a first central aperture adapted and configured to receive therein the alignment feature. The device preferably includes a central pocket that couples to the receiver, the central pocket including a lateral aperture that permits placement therethrough of the protrusion.

X8. Another aspect of the present invention pertains to a member for making a flexible connection between bones. The member preferably includes a connecting member having a first aligning element. The member preferably includes a first separable receiver for a flexible connector, the first receiver having a body including a first protrusion and provisions for a flexible connector. The member preferably includes a head having a pocket that receives therein the first receiver, the pocket including a first lateral aperture that permits placement therethrough of the first protrusion, the head including a second aligning element adapted and configured to couple with the first aligning element, wherein placement of the first receiver within the central pocket permits alignment of the first aligning element with the second aligning element to capture the first and second separable receivers between the head and the connecting member.

Yet other embodiments pertain to any of the previous statements X1, X2, X3, X4, X5, X6, X7 or X8 which are combined with one or more of the following other aspects. It is also understood that any of the aforementioned X paragraphs include listings of individual features that can be combined with individual features of other X paragraphs.

Wherein said coupling means includes a groove extending around the periphery of said head, the groove being adapted and configured to contain the flexible material.

Wherein the flexible member has a diameter, and the width of the groove is greater than the diameter, and the depth of the groove is greater than the diameter.

Wherein said coupling means includes a pair of separated grooves each extending around the periphery of said head, each groove being adapted and configured to contain the flexible material.

Wherein said shaft has an axis, and each groove is substantially perpendicular to the axis.

Wherein said coupling means includes first and second passageways each extending through the interior of said head, each having an entrance for the flexible material and an exit for the flexible material, each entrance and exit being on opposite sides of said head, each of the passageways being smooth and uninterrupted between the corresponding entrance and exit.

Wherein the first and second passageways have uninterrupted side boundaries.

Wherein a portion of the first and second passageways proximate to the neck of said shaft are smooth and continuous.

Wherein the portion of the first and second passageways does not include a blind hole.

Wherein each of the first and second passageways are open to the top surface of said head.

Wherein each of the first and second passageways are enclosed relative to the top surface of said head.

Wherein said coupling means includes first and second passageways each have opposing lateral walls, each lateral wall extending between a corresponding exit and entrance for that passageway, and each lateral wall transitions to the exterior surface of said head proximate to the respective exit or entrance with a radius of curvature greater than ninety degrees.

Wherein said coupling means includes first and second passageways each having an entrance for the flexible material and an exit for the flexible material, each said passageway extending a length from entrance to exit, said head has a maximum width, a minimum width less than the maximum width, and the length of each passageway is less than the minimum width.

Wherein said coupling means includes first and second passageways each having an entrance for the flexible material and an exit for the flexible material, each said passageway extending a length from entrance to exit, said head has a maximum width, and the length of each passageway is less than the maximum width.

Wherein said coupling means includes means for convexly separating the first passageway from the second passageway.

Wherein said convex separating means includes a smooth bump between the first and second passageways.

Wherein said convex separating means includes a smooth ridge between the first and second passageways.

Wherein the top of said head includes an open slot permitting passage of the flexible material into each of the passageways.

Wherein the top of head is closed between passageways, such that a portion of flexible material passing through a passageway cannot be lifted vertically out of the passageway.

Wherein the first and second passageways are substantially parallel.

Wherein the first and second passageways combine in a cross-sectional V-shape with the opened end of the V-shape being directed toward the neck of said shaft.

Wherein said head has a maximum width greater than the outer diameter of the threads.

Wherein said head has a width orthogonal to the maximum width that is greater than the outer diameter of the threads but less than the maximum width.

Wherein said head has a minimum width orthogonal to the maximum width that is less than the maximum width.

Wherein said head has an outer shape that is oblong.

Wherein said shaft, said head, and said coupling means are unitary.

Wherein the outer surfaces of said head are smooth.

Wherein said head has a non-circular outer peripheral shape adapted and configured to receive a driving torque from a driving tool having a complementary inner peripheral shape.

Wherein said head has a distal side adapted and configured for resting on the bone when the anchor is fully inserted into the bone.

Wherein said head has a distal side that is substantially flat

Wherein said connecting means includes a shaft having proximal and distal ends, the distal end including a tip adapted and configured for entry into a hole in a bone, the proximal end including a neck, said shaft including a plurality of threads intermediate of the tip and the neck, the threads being adapted and configured for connection with a vertebrae.

Wherein the plurality of threads have a constant outer diameter.

Wherein said connecting means includes a post adapted and configured to connection to a vertebrae.

Wherein said connecting means includes an adjustable loop adapted and configured for connection around a vertebrae.

Wherein said connecting means includes a hook adapted and configured to connection to a vertebrae.

Whether the flexible material is a suture.

Wherein the flexible material is a tether.

Wherein the flexible material is fabricated from a polymeric compound.

Wherein said head includes smoothly contouring walls defining said first and second passageways, the walls being adapted and configured to permit sliding movement of a tether against the wall without abrasively damaging the tether.

Wherein each said passageway has a smooth elongated cross section shape.

Wherein each first and second cross sectional shape is elongated along a respective first or second axis, and the angle included from the first axis to the second axis is more than about ninety degrees and less than one hundred and twenty degrees.

Wherein each first and second cross sectional shape is elongated along a respective first or second axis, and first and second axes have a V shape with the open side of the V being oriented toward said bone connecting member.

Wherein the apex of the V shape is within said head.

Wherein each said post has a maximum width, said head has a minimum width, and the maximum width is less than the minimum width.

Wherein said coupling means includes first and second passageways each having an entrance for the flexible material and an exit for the flexible material, each said passageway extending a length from entrance to exit, said head has a maximum width, and the length of each passageway is less than the maximum width.

Wherein the top surface of said head includes a central slot having a width sized to permit passage therethrough of the flexible tether.

Wherein each said post includes smoothly contouring walls defining the respective groove, the walls being adapted and configured to permit sliding movement of a tether against the wall without abrasively damaging the tether.

Wherein said peripheral grooves are substantially parallel to each other.

Wherein said head has a peripheral shape that is rounded.

Wherein said head has a peripheral shape that is circular.

Wherein said head has a peripheral shape that is oblong or elliptical.

Wherein the aperture includes two separated passageways and wherein said passing includes guiding one side of the tether loop within one passageway and guiding the other side of the tether loop within the other passageway.

Which further comprises attaching a third tethering head to a third vertebra, the second vertebra being located between the first vertebra and the third vertebra, and looping the flexible tether passed through the second tethering head in a third groove extending around the periphery of the third tethering head.

Wherein the aperture includes two separated passageways and wherein said passing includes lacing the tether loop within one passageway and around a portion of the second tethering head.

Wherein the tether is a first tether, wherein the aperture includes two separated passageways, the extension of the first looped tether is within one passageway and around a portion of the second tethered head, and which further comprises attaching a third tethering head to a third vertebra, the second vertebra being located between the first vertebra and the third vertebra; looping one end of a second flexible tether within the other passageway and around a different portion of the second tethered head, and looping the other end of the second flexible tether in a third groove extending around the periphery of the third tethering head.

Wherein the tether is a first tether, wherein the first groove is a lower groove, the first tethering head including an upper groove, and which further comprises attaching a third tethering head to a third vertebra, looping a second flexible tether in the upper groove extending around the periphery of the first tethering head, extending the looped second tether from the first tethering head to the third tethering head; and coupling the extension of the looped tether to the third tethering head.

Wherein the tether is an endless loop.

Which further comprises attaching together the free ends of a portion of flexible tether and creating an endless loop of tether from the portion after said passing.

Which further comprises attaching together the free ends of a portion of flexible tether and creating an endless loop of tether from the portion before said wrapping.

Which further comprises attaching together the free ends of a portion of flexible tether and creating an endless loop of tether from the portion.

Wherein said separable receiver is a first separable receiver, and which further comprises: a second separable receiver for a flexible connector, said second receiver having a second body including a second protrusion with a second passageway for a flexible connector and including a third central aperture adapted and configured to receive therein the alignment feature; wherein the lateral aperture is a first lateral aperture and said head includes a second lateral aperture spaced apart from the first lateral aperture that permits placement therethrough of the second protrusion; wherein connection of said bone connecting member to a bone aligns said receiver and said head and captures said first separable receiver and said second separable receiver within the central pocket.

Wherein said first lateral aperture is angularly spaced apart from said second lateral aperture by about ninety degrees or less.

Wherein said first lateral aperture is angularly spaced apart from said second lateral aperture by about ninety degrees or more.

Wherein said central pocket has an internal shape, the body of said separable receiver has an external shape, and the external shape is a close fit within the internal shape.

Wherein said alignment feature has an external shape, the first central aperture has an internal shape, and the external shape is a close fit within the internal shape.

Wherein said alignment feature has an external shape, the second central aperture has an internal shape, and the external shape is a close fit within the internal shape.

Wherein said head includes a bone contacting side that includes a plurality of projections adapted and configured to penetration into the bone.

Wherein said bone connecting member includes a head that covers the central pocket.

Wherein said bone connecting member includes a threaded shaft having a lumen therethrough.

Wherein the first lateral aperture and said second lateral aperture are spaced apart.

Wherein said first separable receiver is substantially identical to said second separable receiver.

Wherein said first receiver includes a first secondary alignable feature adapted and configured to mate with the first alignable element, and said second receiver includes a second secondary alignable feature adapted and configured to mate with the first alignable element.

Wherein said connecting member is a threaded fastener adapted and configured for connection to a bone.

Wherein said connecting member is a first connecting member and one of said first connecting member or said head is adapted and configured for connection to a bone connecting member.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A method for flexibly connecting vertebrae, comprising:
    attaching a first tethering head to a first vertebra;
    attaching a second tethering head to the first vertebra spaced apart from the first tethering head;
    attaching a third tethering head to a second vertebra;
    attaching a fourth tethering head to the second vertebra spaced apart from the third tethering head;
    attaching a fifth tethering head to a third vertebra;
    placing a first flexible member in a first groove in the first tethering head;
    placing a second flexible member in a second groove in the second tethering head;
    placing a third flexible member in a third groove in the third tethering head;
    placing a fourth flexible member in a fourth groove in the fourth tethering head;
    connecting the first vertebra to the second vertebra by tethering the first tethering head to the third tethering head with the first flexible member;
    connecting the first vertebra to the second vertebra by tethering the second tethering head to the third tethering head with the second flexible member;
    connecting the second vertebra to the third vertebra by tethering the third tethering head to the fifth tethering head with the third flexible member;
    connecting the second vertebra to the third vertebra by tethering the fourth tethering head to the fifth tethering head with the fourth flexible member; and
    leaving the first tethering head untethered from the fourth tethering head.

2. The method of claim 1, further comprising:
attaching together free ends of the first flexible member and creating a first loop of flexible member before said tethering the first tethering head to the third tethering head with the first flexible member.

3. The method of claim 2, further comprising:
leaving the second tethering head untethered from the fourth tethering head.

4. The method of claim 1, further comprising:
attaching together free ends of the first flexible member and creating a first loop of flexible member before said placing the first flexible member in the first groove in the first tethering head.

5. The method of claim 4, further comprising:
leaving the second tethering head untethered from the fourth tethering head.

6. The method of claim 1, wherein the first flexible member is a loop.

7. The method of claim 6, further comprising:
leaving the second tethering head untethered from the fourth tethering head.

8. The method of claim 1, wherein the second flexible member is a loop.

9. The method of claim 8, further comprising:
leaving the second tethering head untethered from the fourth tethering head.

10. The method of claim 1, wherein said placing the first flexible member in the first groove comprises passing the first flexible member through an opening in a head of the first tethering head.

11. The method of claim 10, further comprising:
leaving the second tethering head untethered from the fourth tethering head.

12. The method of claim 1, further comprising:
leaving the second tethering head untethered from the fourth tethering head.

\* \* \* \* \*